(12) United States Patent
DeShazo et al.

(10) Patent No.: US 11,351,376 B2
(45) Date of Patent: Jun. 7, 2022

(54) PARAMETRIC CHARACTERIZATION OF AN IMPLANTED LEAD SYSTEM ASSOCIATED WITH AN IMPLANTABLE PULSE GENERATOR

(71) Applicant: Advanced Neuromodulation Systems, Inc., Plano, TX (US)

(72) Inventors: Daran DeShazo, Lewisville, TX (US); Steven Boor, Plano, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 224 days.

(21) Appl. No.: 16/783,837

(22) Filed: Feb. 6, 2020

(65) Prior Publication Data

US 2021/0244948 A1    Aug. 12, 2021

(51) Int. Cl.
*A61N 1/36*    (2006.01)
*A61N 1/372*    (2006.01)
*A61N 1/08*    (2006.01)

(52) U.S. Cl.
CPC ....... *A61N 1/36071* (2013.01); *A61N 1/3614* (2017.08); *A61N 1/36157* (2013.01); *A61N 1/36175* (2013.01); *A61N 1/36178* (2013.01); *A61N 1/37241* (2013.01); *A61N 2001/083* (2013.01)

(58) Field of Classification Search
CPC .............. A61N 1/36071; A61N 1/3614; A61N 1/36157; A61N 1/36175; A61N 1/36178; A61N 1/37241; A61N 2001/083; A61N 1/36128; A61N 1/36062
See application file for complete search history.

(56) References Cited

U.S. PATENT DOCUMENTS

| | | |
|---|---|---|
| 7,212,110 B1 | 5/2007 | Martin et al. |
| 7,228,179 B2 | 6/2007 | Campen et al. |
| 7,571,007 B2 | 8/2009 | Erickson et al. |
| 9,844,661 B2 | 12/2017 | Franz et al. |
| 10,279,178 B2 | 5/2019 | Cartledge et al. |
| 2006/0167512 A1 | 7/2006 | Ross et al. |
| 2006/0170486 A1 | 8/2006 | Tranchina et al. |
| 2007/0112402 A1 | 5/2007 | Grill et al. |
| 2009/0048643 A1 | 2/2009 | Erickson et al. |
| 2009/0326608 A1 | 12/2009 | Huynh et al. |
| 2011/0072657 A1 | 3/2011 | Swanson et al. |
| 2013/0289667 A1 | 10/2013 | Wacnik et al. |
| 2014/0336727 A1 | 11/2014 | Perryman et al. |
| 2014/0343564 A1 | 11/2014 | Feler et al. |

(Continued)

FOREIGN PATENT DOCUMENTS

WO    2001093953 A1    12/2001

OTHER PUBLICATIONS

Wei, Xuefeng Frank; "Analysis and Design of Electrodes for Deep Brain Stimulation," Department of Biomedical Engineering, Duke University; 2009.

(Continued)

*Primary Examiner* — Paula J Stice

(57) ABSTRACT

A system and method for extracting ETI load parametric data relative to one or more electrodes of an implanted stimulation lead system associated with an IPG. A Kelvin connection scheme is provided for measuring induced voltages present at stimulated electrodes during a stimulation ramping sequence, which may be used for determining the ETI parametric data using a number of techniques, including, without limitation, a waveform analysis.

25 Claims, 12 Drawing Sheets

(56) References Cited

U.S. PATENT DOCUMENTS

2017/0105653 A1   4/2017   Liu et al.
2018/0008821 A1   1/2018   Gonzalez et al.
2020/0155851 A1   5/2020   Boor et al.

OTHER PUBLICATIONS

ISA/US, International Search Report and Written Opinion of the International Searching Authority, Application No. PCT/US2020/066850, dated Mar. 23, 2021, 6 pgs.

PARAMETRIC CHARACTERIZATION OF AN IMPLANTED LEAD SYSTEM ASSOCIATED WITH AN IMPLANTABLE PULSE GENERATOR

TECHNICAL FIELD

The present disclosure generally relates to implantable pulse generators and circuitry associated therewith. More particularly, and not by way of any limitation, the present disclosure is directed to a system and method for facilitating electrical load parametric characterization of an implanted lead system associated with an implantable pulse generator used in stimulation therapy.

BACKGROUND

The use of electronic stimulation systems to control pain or other indications, or to otherwise provide therapy, by nerve or muscle stimulation has been in use for a number of years. For example, spinal cord stimulation (SCS) is a technique that has been used for pain management since the 1960s. Stimulation systems may also be used in stimulating areas other than the spinal cord, such as for deep brain stimulation, muscle stimulation, etc.

Stimulation systems often comprise a pulse generator coupled to one or more implanted therapy delivery leads having a plurality of electrodes disposed in an area in which neurostimulation is desired. Alternatively, stimulation systems may comprise a micro-stimulation system in which a small implantable housing having electrodes thereon includes a pulse generator, wherein the entire micro-stimulation system is disposed in an area in which neurostimulation is desired. Of course, all or a portion of a stimulation system need not be implanted into a body to provide a desired therapy.

A stimulation system pulse generator may be provided in various configurations, such as a totally implanted pulse generator (IPG) or a radio frequency (RF)-based system. A typical IPG configuration comprises a surgically implanted, internally-powered pulse generator and a multi-electrode lead. A typical RF system configuration comprises a surgically implanted passive receiver and leads, and a transmitter which is worn externally. In operation, the transmitter communicates, through an RF signal, to the implanted receiver to provide stimulation energy and control.

In an SCS application, lead electrodes which are used with an example pulse generator, such as any of the foregoing pulse generators, to deliver a particularized electric field via stimulation to a specific region of the spinal cord or surrounding tissue are considered as the "active" electrodes of the IPG for therapy delivery; unused or "inactive" electrodes are the ones not used for stimulation therapy. Applying such an electric field with the active electrodes across one or more nerve bundles and/or nerve roots, if properly directed and produced at the necessary levels, can "mask" certain forms of chronic pain in a phenomenon referred to as "paresthesia". Similarly, applying an electric field across other tissue, such as muscle or brain matter, near which such electrodes are disposed may provide a desired therapy. The focus, characteristics and intensity of the generated electric field are determined by the electrode configuration (the polarity, if any, assumed by each electrode) and the properties of an electric pulse waveform, which may generally include a stimulation frequency, a stimulation pulse width, a stimulation amplitude, discharge method, and phase information, etc. (collectively "stimulation settings" or "stimsets").

Chronically implantable electrical stimulation mechanisms have been the focus of advanced physiological engineering research for the past few decades. With the advent of microelectronics, it has become imperative to investigate the criticality of safe functional electrical stimulation for large electrode arrays since stimulation electrode characteristics can change due to electrode dissolution/deterioration during prolonged use. Structural damage can occur if there is exposure to electrode potential much higher than applicable electrochemical windows associated with a tissue interface. Moreover, with large stimulation arrays employed in certain applications, monitoring the status of different electrodes becomes challenging.

Whereas advances in IPG systems and associated stimulation circuitry for use in various therapy applications continue to grow apace, several lacunae remain, thereby requiring further innovation as will be set forth hereinbelow.

SUMMARY

Embodiments of the present patent disclosure are broadly directed to implantable pulse generators or other medical devices (IPG/IMD), systems and associated circuitry wherein various types of Kelvin connection schemes may be provided for effectuating diagnostic voltage measurements with respect to one or more electrodes of a stimulation lead system associated with an IMG/IMD system. A system and method is provided for extracting electrical load parametric data relative to the electrode/tissue interface (ETI) equivalent circuit arrangement for an IMD's lead electrode system implanted proximate to a patient's tissue. One or more Kelvin connection paths may be utilized for measuring induced voltages developed at stimulated electrodes during a stimulation ramping sequence. In some embodiments, a ramping sequence for the stimulation parameters (e.g., stimulation current pulse width, amplitude, etc.) may be commenced when therapy is initially turned on for the patient, wherein one or more stimulation parameters are incrementally increased to a target therapy setting. In some embodiments, a ramping sequence may involve incrementally decreasing the stimulation parameters from an applied setting when therapy is deactivated. Measured voltage data obtained at different settings may be used for determining the ETI parametric data based on a waveform analysis.

In one aspect, an embodiment of a method is disclosed for characterizing an ETI circuit representation associated with a lead system of an IPG/IMD implanted in a patient for providing stimulation therapy. The claimed method comprises, inter alia, obtaining voltage measurements at an electrical node associated with at least one electrode implanted in the patient during at least one of a ramping up sequence or a ramping down sequence of a stimulation therapy with respect to the at least one electrode of the lead system. A voltage-to-time functional relationship is obtained based on the voltage measurements. Electrical load parameters associated with an equivalent circuit of the ETI of the at least one electrode may be extracted from the voltage-to-time relationship using a number of techniques. In one embodiment, the method may further include identifying a substantially step-wise function portion, a linear function portion and a nonlinear function portion of the voltage-to-time relationship. A bulk patient resistance ($R_S$) of the equivalent ETI circuit associated with the at least one electrode may be determined from the substantially step-wise function portion of the voltage-to-time relationship. At least one of a double-layer capacitance ($C_{DL}$), a direct current (DC) blocking capacitance ($C_{DC}$), and an equivalent series capacitance ($C_{EQ}$) of the equivalent ETI circuit associated with the at least one electrode may be determined from the linear function portion of the voltage-to-time relationship. A Faradaic resistance ($R_F$) of the equivalent ETI circuit associated with the at least one electrode may be determined from one or more piecewise linear approximations of the nonlinear function portion of the voltage-to-time relationship.

In other aspects, embodiments of an IMD/IPG and/or a biostimulation system is disclosed wherein diagnostic circuitry operative with a Kelvin connection arrangement is configured to facilitate voltage measurements and extraction of ETI parametric data under suitable processor control during a stimulation ramping sequence. In an example implementation, terminals of a DC blocking stimulation capacitor or an AC-coupling sense capacitor associated with an inactive electrode of the lead system may be configured as one Kelvin connection terminal or node of a measurement circuit path whereas a counter Kelvin connection terminal or node with respect to a select active electrode is effectuated across the electrode/tissue interface using either a DC blocking stimulation capacitor or an AC-coupling sense capacitor provided therewith.

Example embodiments of the present patent disclosure may be advantageously configured to obtain in vivo ETI parametric data, which allows real-time monitoring and/or adjustment of a target therapy setting, thereby optimizing stimulation therapy provided to the patient. By leveraging stimulation parameter ramping during therapy initialization and/or deactivation, which may be typically employed to mitigate unpleasant "shocking" sensations for the patient, the diagnostic information can be obtained without any interference in the normal delivery of therapy to the patient. Moreover, such optimization can ensure patient safety and electrode integrity, minimize patient discomfort, as well as potentially help monitor lead network integrity and extend the device battery longevity, thereby resulting in improved patient therapy.

Additional/alternative features and variations of the embodiments will be apparent in view of the following description and accompanying Figures.

BRIEF DESCRIPTION OF THE DRAWINGS

Embodiments of the present disclosure are illustrated by way of example, and not by way of limitation, in the Figures of the accompanying drawings in which like references indicate similar elements. It should be noted that different references to "an" or "one" embodiment in this disclosure are not necessarily to the same embodiment, and such references may mean at least one. Further, when a particular feature, structure, or characteristic is described in connection with an embodiment, it is submitted that it is within the knowledge of one skilled in the art to effectuate such feature, structure, or characteristic in connection with other embodiments whether or not explicitly described.

The accompanying drawings are incorporated into and form a part of the specification to illustrate one or more exemplary embodiments of the present disclosure. Various advantages and features of the disclosure will be understood from the following Detailed Description taken in connection with the appended claims and with reference to the attached drawing Figures in which:

DETAILED DESCRIPTION

Figure 1A:
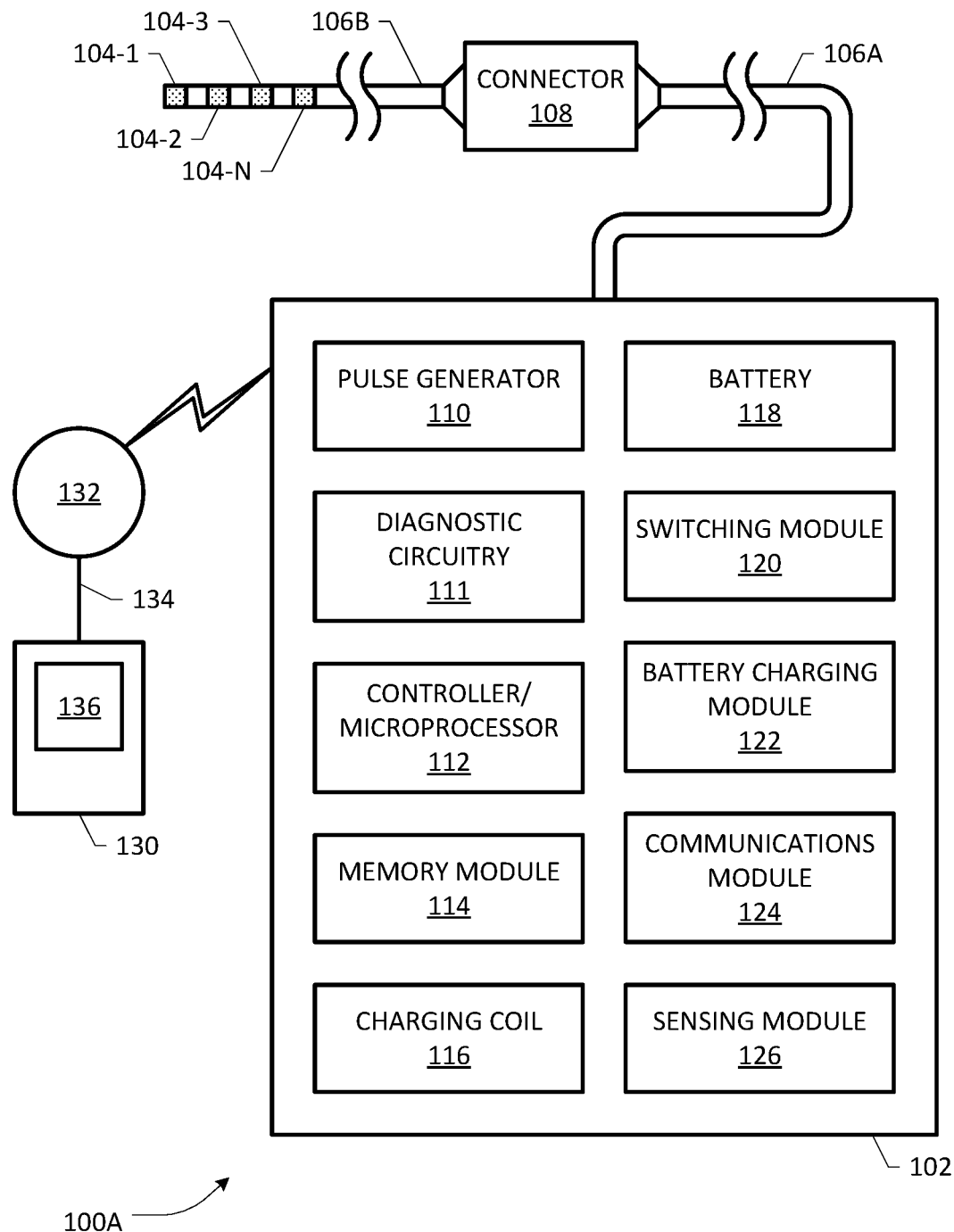
FIG. 1A depicts an example biostimulation system wherein one or more embodiments of a diagnostic scheme of the present disclosure may be practiced for purposes of real-time extraction of electrical load parameters of implanted lead electrodes in accordance with the teachings herein.

In the description herein for embodiments of the present disclosure, numerous specific details are provided, such as examples of circuits, devices, components and/or methods, to provide a thorough understanding of embodiments of the present disclosure. One skilled in the relevant art will recognize, however, that an embodiment of the disclosure can be practiced without one or more of the specific details, or with other apparatuses, systems, assemblies, methods, components, materials, parts, and/or the like. In other instances, well-known structures, materials, or operations are not specifically shown or described in detail to avoid obscuring aspects of embodiments of the present disclosure.

Accordingly, it will be appreciated by one skilled in the art that the embodiments of the present disclosure may be practiced without such specific components. It should be further recognized that those of ordinary skill in the art, with the aid of the Detailed Description set forth herein and taking reference to the accompanying drawings, will be able to make and use one or more embodiments without undue experimentation.

Additionally, terms such as "coupled" and "connected," along with their derivatives, may be used in the following description, claims, or both. It should be understood that these terms are not necessarily intended as synonyms for each other. "Coupled" may be used to indicate that two or more elements, which may or may not be in direct physical or electrical contact with each other, co-operate or interact with each other. "Connected" may be used to indicate the establishment of communication, i.e., a communicative relationship, between two or more elements that are coupled with each other. Further, in one or more example embodiments set forth herein, generally speaking, an electrical element, component or module may be configured to perform a function if the element may be programmed for performing or otherwise structurally arranged to perform that function.

Some embodiments described herein may be particularly set forth in the context of an implantable pulse generator (IPG) for generating electrical stimulation for application to a desired area of a body or tissue based on a suitable stimulation therapy application, such as a spinal cord stimulation (SCS) system. However, it should be understood that example circuitry and methods of operation disclosed herein are not limited thereto, but have broad applicability, including but not limited to different types of implantable devices such as neuromuscular stimulators and sensors, dorsal root ganglion (DRG) stimulators, deep brain stimulators, cochlear stimulators, retinal implanters, muscle stimulators, tissue stimulators, cardiac stimulators, gastric stimulators, and the like, including other bioelectrical sensors and sensing systems, which may be broadly referred to as "biostimulation" applications and/or implantable medical devices (IMDs) for purposes of the present disclosure. Moreover, example circuitry and methods of operation disclosed herein are not limited to use with respect to an IPG or any particular form of IPG. For example, some embodiments may be implemented with respect to a fully implantable pulse generator, a radio frequency (RF) pulse generator, an external pulse generator, a micro-implantable pulse generator, inter alia.

Referring to FIG. 1A in particular, depicted therein is a biostimulation system or IMD system 100A wherein one or more embodiments of a diagnostic scheme of the present patent disclosure may be practiced for effectuating in vivo voltage measurements using a Kelvin connection arrangement for purposes of real-time extraction of electrical load parameters of an electrode/tissue interface (ETI) equivalent circuit arrangement associated with lead electrodes in accordance with the teachings herein. By way of illustration, system 100A may be adapted to stimulate spinal cord tissue, peripheral nerve tissue, deep brain tissue, DRG tissue, cortical tissue, cardiac tissue, digestive tissue, pelvic floor tissue, or any other suitable biological tissue of interest within a patient's body, as noted above. System 100A includes an implantable pulse generator (IPG) or IMD 102 that comprises a diagnostic circuit module 111 adapted to effectuate Kelvin connections with one or more electrodes of an implantable lead system for measuring voltages associated with the stimulated electrodes in connection with electrical load characterization as will be set forth in additional detail further below. In one example embodiment, IPG 102 may be implemented as having a metallic housing or can that encloses a controller/processing block or module 112, pulse generating circuitry 110, a charging coil 116, a battery 118, a far-field and/or near field communication block or module 124, battery charging circuitry 122, switching circuitry 120, sensing circuitry 126, a memory module 114, and the like. Controller/processor module 112 typically includes a microcontroller or other suitable processor for controlling the various other components of IPG/IMD 102. Software/firmware code may be stored in memory 114 of IPG 102, which may be integrated with the controller/processor module 112, and/or other suitable application-specific storage components (not particularly shown in this FIG.) for execution by the microcontroller or processor 112 and/or other programmable logic blocks to control the various components of the device for purposes of an embodiment of the present patent disclosure.

In one arrangement, IPG 102 may be coupled to a separate or an attached extension component 106A for providing electrical and physical connectivity to an implantable lead system 106B via a lead connector 108, wherein a distal end of the lead 106B includes a plurality of electrodes 104-1 to 104-N. Where the extension component 106A is provided as a separate component, the extension component 106A may connect with a "header" portion of IPG 102 as is known in the art. If the extension component 106A is integrated with IPG 102, internal electrical connections may be made through respective conductive components. In general, electrical pulses are generated by the pulse generating circuitry 110 under the control of processing block 112, and are provided to the switching circuitry 120 that is operative to selectively connect to electrical outputs of the IPG device, which are ultimately coupled to the electrodes 104-1 to 104-N at a distal end of the lead system 1066 via respective electrical conductive traces.

In one arrangement, lead electrodes 104-1 to 104-N may be positioned along an axis of the lead 106B, with an angular offset such that the lead electrodes 104-1 to 104-N do not overlap. The lead electrodes 104-1 to 104-N may be in the shape of a ring such that each lead electrode continuously covers the circumference of the exterior surface of the lead 106B. Typically, the lead electrodes 104-1 to 104-N are separated from each other by non-conducting portions of the lead 106B, which electrically isolate each lead electrode 104-1 to 104-N from an adjacent lead electrode 104-1 to 104-N. The non-conducting portions of the lead 106B may include one or more insulative materials and/or biocompatible materials to allow the lead 106B to be implantable within the patient. Non-limiting examples of such materials include polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane, or the like compositions.

Additionally or alternatively, electrodes 104-1 to 104-N may be in the shape of a split or non-continuous ring such that the stimulation pulse(s) may be emitted in a manner so as to create an electric field emanating in an outward radial direction adjacent to the lead electrodes 104-1 to 104-N. Examples of lead electrodes 104-1 to 104-N and associated fabrication processes are disclosed in one or more of the following: (i) U.S. Patent Application Publication No. 2011/0072657, entitled, "METHOD OF FABRICATING STIMULATION LEAD FOR APPLYING ELECTRICAL STIMULATION TO TISSUE OF A PATIENT"; and (ii) U.S. Patent Application Publication No. 2018/0008821, entitled, "IMPLANTABLE THIN FILM DEVICES", each of which is incorporated herein by reference.

It should be noted the lead electrodes 104-1 to 104-N may be in various other formations, for example, in a planar formation, in an array or grid, etc. on a paddle structure as disclosed in U.S. Patent Application Publication No. 2014/0343564, entitled, "PADDLE LEADS FOR NEUROSTIMULATION AND METHOD OF DELIVERYING THE SAME", which is incorporated herein by reference.

In one arrangement, the lead system 106B (as well as extension 106A where provided) may comprise a lead body of insulative material encapsulating a plurality of conductors within the material that extend from a proximal end (that is proximate to IPG 102) to the distal end of the lead body containing the lead electrodes 104-1 to 104-N. The conductors or conductive traces are operative to electrically couple the lead electrodes 104-1 to 104-N to a corresponding plurality of terminals (not shown) of the lead system 106A/B. In general, the terminals are adapted to receive electrical pulses from the pulse generation and switching circuitry of IPG 102, which are propagated via the corresponding conductive traces to at least a portion of the lead electrodes 104-1 to 104-N that are adapted to apply the pulses to a desired stimulation target of the patient depending on the particular stimulation therapy application. Also, sensing of physiological or bioelectrical signals may occur through the lead electrodes 104-1 to 104-N, corresponding conductors, and associated terminals. By way of illustration, an example embodiment of the stimulation system 100A may be provided with a plurality of lead electrodes 104-1 to 104-N comprising four electrodes, eight electrodes, etc., although any suitable number of electrodes (as well as corresponding conductive traces and terminals) may be provided in a lead system. Additionally or alternatively, various sensors (e.g., a position detector, temperature sensor, one or more electrochemical sensors, a radiopaque fiducial, etc.) may be located near the distal end of the lead 106B and electrically coupled to terminals through associated conductors within the lead body.

Although not required for all embodiments, the lead body of the implantable lead system 106A/106B may be fabricated to flex and elongate upon implantation or advancing within or relative to the tissue (e.g., nervous tissue) of the patient towards the stimulation target to account for movement of the patient during or after implantation. Fabrication techniques and material characteristics for "body compliant" leads are disclosed in greater detail in U.S. Pat. No. 9,844,661, entitled "COMPLIANT ELECTRICAL STIMULATION LEADS AND METHODS OF FABRICATION", which is incorporated herein by reference.

An example implementation of the components within IPG 102, such as, e.g., processor and associated charge control circuitry for an IPG, is described in U.S. Pat. No. 7,571,007, entitled "SYSTEMS AND METHODS FOR USE IN PULSE GENERATION", which is incorporated herein by reference. An example implementation of circuitry for recharging a rechargeable battery (e.g., battery charging circuitry 122) of an IPG using inductive coupling and external charging circuits is described in U.S. Pat. No. 7,212,110, entitled "IMPLANTABLE DEVICE AND SYSTEM FOR WIRELESS COMMUNICATION", which is incorporated herein by reference. Still further, an example implementation of "constant current" pulse generating circuitry (e.g., at least a portion of pulse generating circuitry 110) is provided in U.S. Patent Application Publication No. 2006/0170486 entitled "PULSE GENERATOR HAVING AN EFFICIENT FRACTIONAL VOLTAGE CONVERTER AND METHOD OF USE", which is incorporated herein by reference. One or multiple sets of such circuitry may be provided within IPG 102 operating in association with a current control module for providing stimulation across a select number of electrodes. Different stimulation pulses on different lead electrodes selected from electrodes 104-1 to 104-N may be generated using consecutively generated pulses according to a "multi-stimset program" as is known in the art. Complex pulse parameters may be employed such as those described in U.S. Pat. No. 7,228,179, entitled "METHOD AND APPARATUS FOR PROVIDING COMPLEX TISSUE STIMULATION PATTERNS", and International Patent Publication Number WO 2001/093953, entitled "NEUROMODULATION THERAPY SYSTEM", which are incorporated herein by reference. Alternatively, multiple sets of such stimulation circuitry may be employed to provide high frequency pulse patterns (e.g., tonic stimulation waveform, burst stimulation waveform, and the like) that include generated and delivered stimulation therapy through one or more leads 104-1 to 104-N as is also known in the art. Various sets of parameters may define the pulse characteristics and pulse timing for the pulses applied to the various lead electrodes as is known in the art. Although constant current pulse generating circuitry is contemplated for some embodiments, any other suitable type of pulse generating circuitry may be employed such as constant voltage pulse generating circuitry.

In an example implementation of IPG 102, sensing circuitry 126 may be provided, preferably adapted to measure a suitable electric parameter or transduced characteristic (e.g., voltage, current, capacitance, etc.) over a configurable time associated with the stimulation target or tissue through at least one of the electrodes proximate to the stimulation target, e.g., electrodes configured to operate as biosensing inputs, wherein such "sensing" electrodes may be coupled to the sensing circuitry 126 via suitable alternating current (AC)-coupling capacitors. In an example embodiment, the sensing circuitry 126 may measure an evoked compound activation potential (ECAP) waveform from an $A\beta$ sensory fiber or spinal cord. Optionally, the sensing circuitry 126 may store the measured/sensed electric data in memory 114. Furthermore, the diagnostic circuitry 111 may be configured to interoperate with the sensing circuitry 126 and pulse generation and switching functionalities of the IPG device 102 for effectuating diagnostic voltage measurements as well as in vivo electrical load characterization of one or more stimulated electrodes of the implanted lead system, which will be set forth further below in additional detail.

An external device 130 may be implemented to charge/recharge the battery 118 of IPG 102 (although a separate recharging device could alternatively be employed), to access memory 114, and/or to program or reprogram IPG 102 with respect to the stimulation set parameters including pulsing specifications, ramping sequences, etc., while implanted within the patient. In alternative embodiments, however, separate programmer devices may be employed for charging and/or programming the IPG 102 device and/or any programmable components thereof. An example embodiment of the external device 130 may be a processor-based system that possesses wireline and/or wireless communication capabilities, e.g., a tablet, smartphone, laptop computer, handheld computer, a personal digital assistant (PDA), or any smart wearable device and smart digital assistant device, etc. Software may be stored within a non-transitory memory of the external device 130, which may be executed by the processor to control the various operations of the external device 130. A connector or "wand" 134 may be electrically coupled to the external device 130 through suitable electrical connectors (not specifically shown), which may be electrically connected to a telemetry component 132 (e.g., inductor coil, RF transceiver, etc.) at the distal end of wand 134 through respective communication links that allow bi-directional communication with IPG 102. Optionally, in some embodiments, the wand 134 may comprise one or more temperature sensors for use during charging operations.

In one general scenario, a user (e.g., a doctor, a medical technician, or the patient) may initiate communication with IPG 102 by placing the wand 134 proximate to the stimulation system 100A. Preferably, the placement of the wand 134 allows the telemetry system to be aligned with the far-field and/or near field communication circuitry 124 of IPG 102. The external device 130 preferably provides one or more user interfaces 136 (e.g., touch screen, keyboard, mouse, buttons, scroll wheels or rollers, or the like), allowing the user to operate IPG 102. The external device 130 may be controlled by the user through the user interface 136, allowing the user to interact with IPG 102, including, e.g., dynamically configuring electrodes for effectuating different Kelvin connection schemes, effectuating programmatic control for facilitating voltage measurements and extraction of electrical load parameters based on applicable equivalent ETI circuit models, etc. as will be set forth further below. Further, the user interface 136 may permit the user to move electrical stimulation along and/or across one or more of the lead(s) 106A using different lead electrode combinations selected from electrodes 104-1 to 104-N, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME", which is incorporated herein by reference. Optionally, the user interface 136 may permit the user to designate which electrodes 104-1 to 104-N are to stimulate (e.g., emit current pulses, in an anode state or in a cathode state), or not selected to stimulate (i.e., remain inactive or floating, i.e., "unused"), with respect to a potential stimulation target, to measure/sense tissue electrical parameters, or the like. As used herein "stimulation" refers to the application of an electrical signal to a target body tissue, regardless of the effect that signal is intended to produce. Additionally or alternatively, the external device 130 may access or download the electrical measurements from the memory 114 acquired by the sensing circuitry 126 and/or diagnostic circuitry 111.

In some implementations, the external device 130 may permit operation of IPG 102 according to one or more spinal cord stimulation (SCS) programs or therapy applications to treat the patient. Each SCS program may include one or more sets of stimulation parameters of the pulse including pulse amplitude, stimulation level, pulse width, pulse frequency or inter-pulse period, pulse repetition parameter (e.g., number of times for a given pulse to be repeated for respective stimulation sets or stimsets during execution of program), biphasic pulses, monophasic pulses, etc. IPG 102 modifies its internal parameters in response to the control signals from the external device 130 to vary the stimulation characteristics of the stimulation therapy transmitted through the lead system 106A/106B to the tissue of the patient. Example neurostimulation (NS) systems, stimsets, and multi-stimset programs are set forth in U.S. Pat. No. 7,228,179, entitled "METHOD AND APPARATUS FOR PROVIDING COMPLEX TISSUE STIMULATION PATTERNS", and International Patent Publication Number WO 2001/093953, entitled "NEUROMODULATION THERAPY SYSTEM", which are incorporated hereinabove by reference.

It will be appreciated that although example lead system 106A/B shown in FIG. 1A is illustrated with a single implantable lead, the teachings herein are not necessarily limited thereto and an example embodiment of the present invention may involve a lead system comprising two or more implantable leads, with each lead having a respective plurality of electrodes, wherein different types of Kelvin connection paths may implemented across a given equivalent ETI circuit model for measuring voltages, and hence electrical load characterization, in accordance with the teachings herein.

It is known that in providing a stimulation signal to a target body tissue, an accumulation of continuous or net charge at the electrode/tissue interface may occur, resulting in a residual voltage, which may not only dynamically affect the electrical characteristics of stimulation pulses being applied but also contribute to deterioration of lead electrode integrity. To maintain charge balance, accordingly, some arrangements of IPG 102 may include output coupling capacitors between the output circuits of the pulse generation/switching circuitry and the electrodes to block errant continuous direct current (DC) and serve as "passive" charge balancing components for the electrical signals being applied to the tissue. In such arrangements, charge built up on the electrodes during stimulation may be offset by use of such output coupling capacitors (DC blocking stimulation capacitors), and may be discharged when delivery of a portion of the electrical signal is completed, e.g., typically after delivery of an individual pulse in a stimulation signal. A "discharge phase" may be observed for a period, for example, after a monophasic stimulation phase. In one arrangement, the stimulation phase and the discharge phase taken together may be considered a charge-balanced pulse in a signal comprising a plurality of such pulses. Even in such arrangements, however, there may be a gradual buildup of residual voltage across the DC blocking stimulation capacitors over time, depending on the frequency and type of pulsing schemes and associated stimsets used, in addition to the charge/voltage buildup at the ETI of an implantable lead system.

Figure 1B:
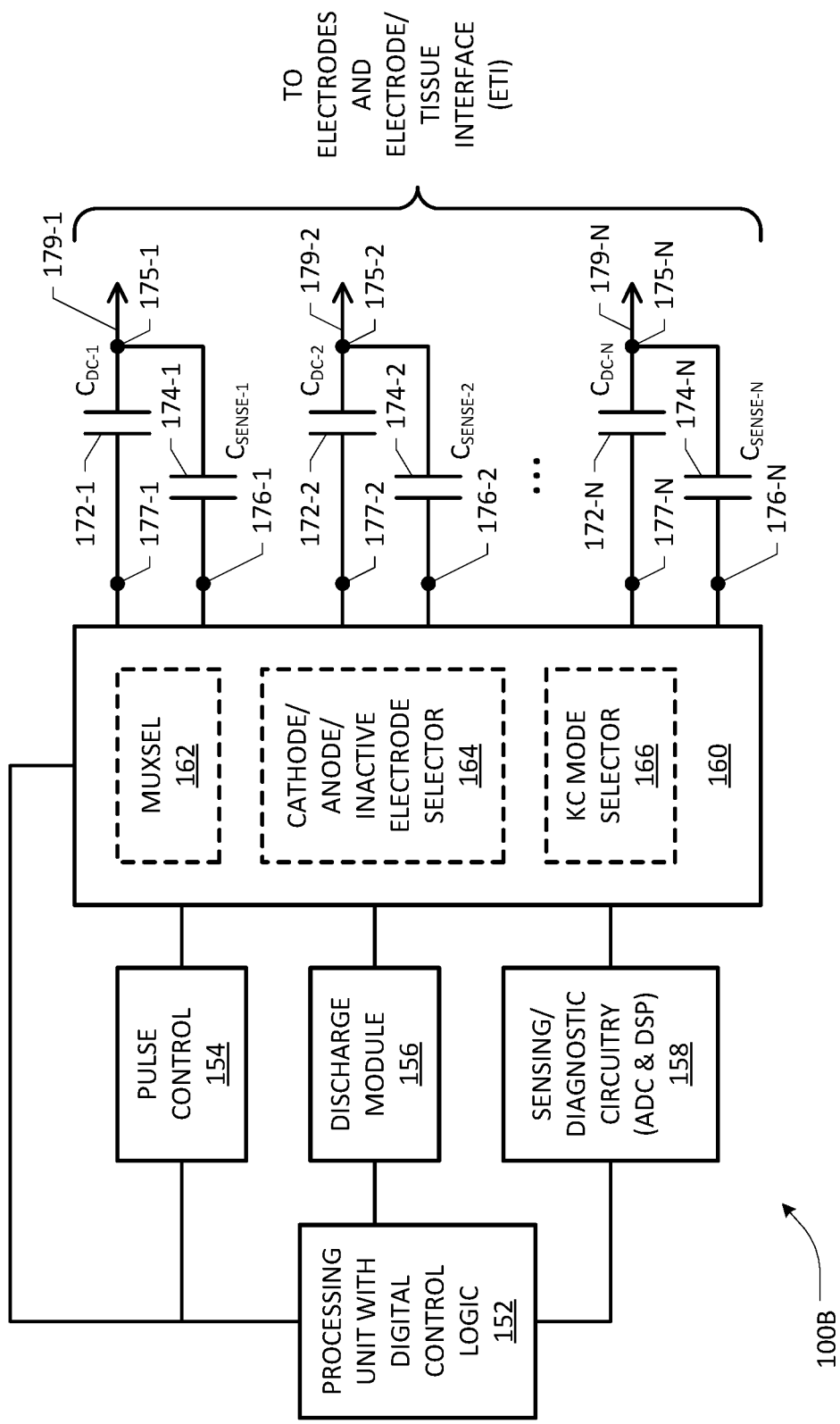
FIG. 1B depicts a pulse generator portion having diagnostic circuitry and associated lead electrode capacitor arrangement according to an embodiment of the present disclosure.

Turning to FIG. 1B, depicted therein is a pulse generator portion 100B having diagnostic circuitry and associated lead electrode capacitor arrangement for purposes of an embodiment of the present disclosure. One skilled in the art will recognize upon reference hereto that various functionalities associated with example blocks shown as part of the pulse generator portion 100B may be distributed and/or integrated among one or more blocks, subsystems and/or modules described hereinabove with respect to FIG. 1A. Consistent with the description set forth previously, a processing unit 152 having or associated with suitable digital control logic is operatively coupled to pulse control module 154, discharge module 156 and sensing/diagnostic circuitry 158 for facilitating various functionalities including but not limited to voltage measurements, active discharge cycling, electrode selection and configuration, etc., as well as electrical load characterization of an equivalent ETI circuit arrangement associated with a lead system under appropriate programmatic control. An input/output (I/O) interface block 160 is operatively coupled to a plurality of lead connectors 179-1 to 179-N comprising a lead system interfaced with respective electrodes and associated ETI that may be represented as circuitry based on known or heretofore unknown charge-transfer mechanisms or models (not shown in this FIG.). Each lead connector 179-1 to 179-N may be provided with a DC blocking stimulation capacitor ($C_{DC}$) as well as an AC-coupling sense capacitor ($C_{SENSE}$) for facilitating direct current flow blocking and AC-coupling functionality with respect to the corresponding electrode that may be configured to operate as a stimulation node or a sensing node. By way of illustration, DC blocking stimulation capacitor $C_{DC-1}$ 172-1 and sense capacitor $C_{SENSE-1}$ 174-1 are coupled to lead connector 179-1 such that two interface terminals 177-1 and 176-1 are effectuated with respect to the lead circuitry of the interface block 160. Sense capacitor $C_{SENSE-1}$ 174-1 is shunted across $C_{DC-1}$ 172-1 such that an intermediate tap or node 175-1 is effectuated on the lead connector 179-1. Likewise, remaining lead connectors 179-N may be provided with respective $C_{SENSE-N}$ 174-N shunted across $C_{DC-N}$ 172-N to facilitate two interface terminals or nodes 177-N and 176-N for each corresponding lead electrode connector. As will be seen below, such an arrangement facilitates a Kelvin connection path via the sense capacitor interface terminal 176-N with respect to each active electrode for purposes of voltage measurement. Although the illustrated embodiment of FIG. 1B exemplifies an arrangement where each lead connector is provided with a corresponding sense capacitor, it should be appreciated that other arrangements may be realized within the scope of the present patent disclosure where not all lead connectors are coupled to respective sense capacitors.

Interface block 160 may include appropriate multiplexing and selection circuitry 162, anode/cathode/inactive electrode selection circuitry 164 and Kelvin connection (KC) mode selection circuitry 166 for effectuating various types of Kelvin connection schemes for measurement purposes while different electrodes of a lead system may be selectively configured for stimulation (e.g., anodic or cathodic stimulation), sensing, or designating unused/inactive states, etc., with appropriate electrical connections being made within an IPG device accordingly relative to the various components therein, under suitable programmatic control as needed. Example diagnostic circuitry 158 may comprise suitable analog-to-digital converter (ADC) circuitry configured for digital voltage measurement and associated signal processing using known voltage measurement techniques. As such, voltage measurement circuitry can be external and/or internal, on-board or off-board, and/or may be coupled to other measurement devices. Responsive to residual voltage measurements, active charge balancing may be effectuated by applying a discharge pulse of opposite polarity at a select electrode to reduce or eliminate the individual residual voltages of select electrodes by using discharge cycle module 156 in conjunction with switch circuitry under suitable programmatic control. Additional details regarding configuring lead electrodes as cathodes or anodes, either during stimulation or for discharging, may be found in may be found in U.S. Patent Application Publication No. 2009/0048643, entitled "METHOD FOR PROVIDING MULTIPLE VOLTAGE LEVELS DURING PULSE GENERATION AND IMPLANTABLE PULSE GENERATING EMPLOYING THE SAME", which is hereby incorporated herein by reference.

Figure 1C:
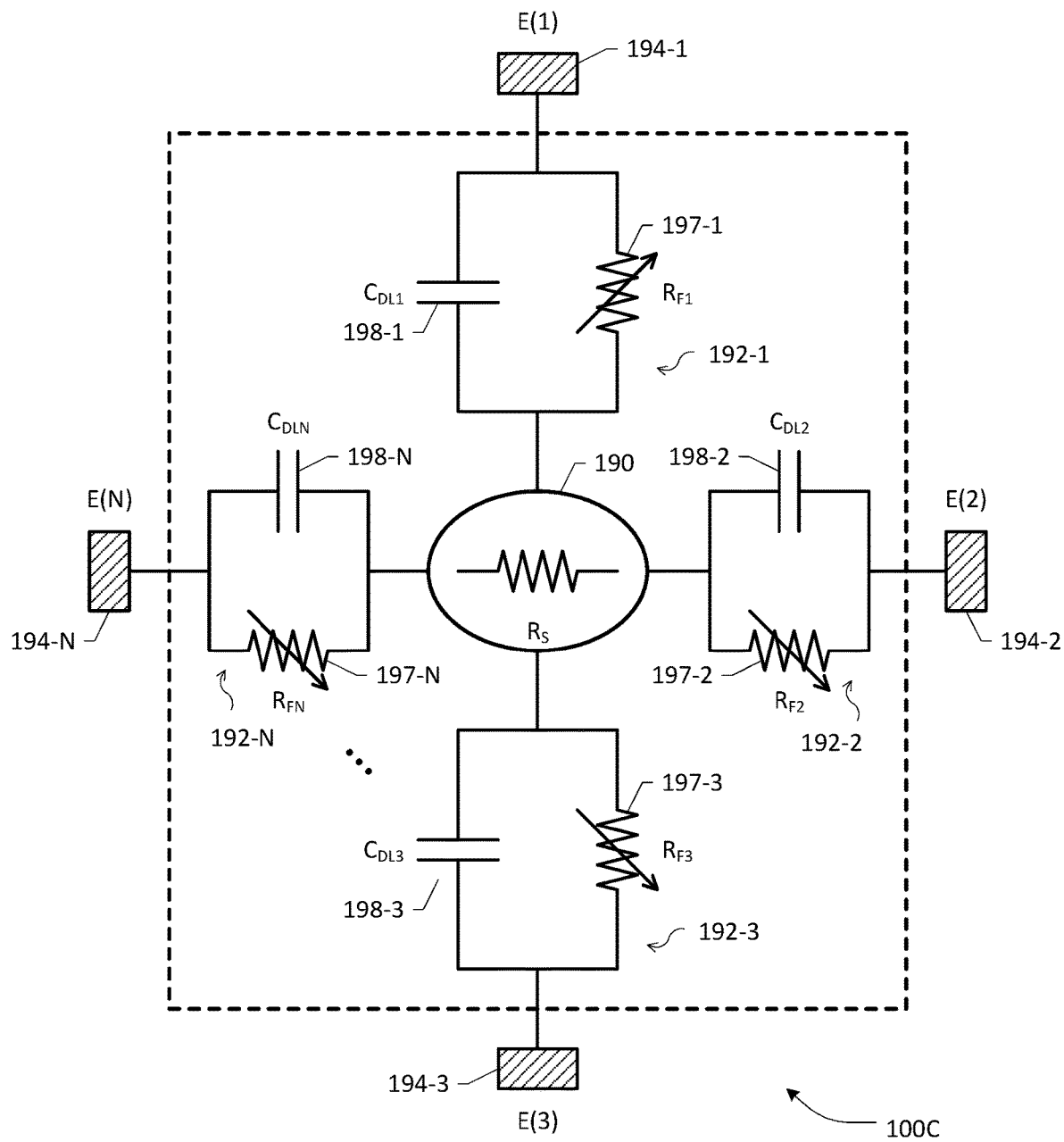
FIG. 1C depicts a generalized electrode/tissue interface (ETI) equivalent circuit arrangement for an IMD's lead electrode system that may be characterized according to an embodiment of the present disclosure.

When an electrode is placed near tissue, current flow is determined by the flow of electrons in the electrode and flow of ions in the tissue. The electrode/electrolyte (i.e., tissue) interface (EEI or ETI; also sometimes referred to as electrode/patient interface or EPI) is typically modeled in accordance with a linear lumped element charge transfer model (e.g., Randles equivalent circuit of the electrode-electrolyte interface), involving a series of lumped resistor elements coupled with a shunt capacitance that models the double layer of charge at the interface. FIG. 1C depicts a generalized ETI equivalent circuit arrangement 100C for an IMD's lead electrode system that may be characterized according to an embodiment of the present disclosure. In the illustrated arrangement 100C, the solution resistance, $R_S$, is representative of the bulk electrolyte, which models the tissue or patient resistance, $R_{PATIENT}$, as a pure resistive component 190 disposed across electrodes E(1) 194-1 to E(N) 194-N. With respect to each electrode, a double-layer capacitance or $C_{DL}$ models the double layer of charge at the interface, which is coupled in parallel to a charge transfer resistance $R_{CT}$, also referred to as Faradaic resistance ($R_F$), across the interface. Faradaic resistance, $R_F$, in parallel with the capacitance, $C_{DL}$, accounts for the conduction of charge through the interface, which can occur through various mechanisms, e.g., typically through oxidation-reduction reactions at the electrode for efficient operation of stimulation electrodes. Reference numerals 192-1 to 192-N shown in FIG. 1C accordingly refer to equivalent circuit representations of ETIs associated with corresponding electrodes 194-1 to 194-N, respectively, wherein $C_{DL1}$ 198-1 to $C_{DLN}$ 198-N and $R_{F1}$ 197-1 to $R_{FN}$ 197-N are illustrative of the respective lumped capacitive and resistive components thereof. Whereas more complex models of the electrode/tissue interface may be used, the foregoing charge transfer model is illustrated herein without necessarily being limited thereto for purposes of exemplifying how Kelvin connection paths may be advantageously effectuated for facilitating individual electrode voltage measurements that may be used in electrical load characterization of the individual electrodes of a lead system. A "Kelvin connection" for purposes of the present patent disclosure is a circuit arrangement that allows avoiding voltage drops (thereby current flows) in circuit segments in a measurement or instrumentation circuit path that may interfere with or confound measurement variables. Example embodiments disclosed herein facilitate such connection arrangements by employing either unused DC blocking stimulation capacitor paths and/or AC-coupling sense capacitor paths associated with respective electrodes (shown in FIG. 1B) in a number of schemes or combinations (collectively, "modes") that may be selectively configured depending on a particular implementation in order to isolate the respective capacitive components of an ETI load (e.g., depending on whether DC blocking capacitors ($C_{DC}$) are used in a voltage measurement path).

It will be appreciated that optimal stimulation therapy settings for an individual patient therapy application may vary over time and may require taking into account the dynamic variability typically present in any biostimulation therapy due to, e.g., the variation of capacitive components implemented in an IPG lead system, electrophysiological/electrochemical variability within a patient tissue over time as well as across different patients (i.e., inter-patient variability), in addition to the temporal variability of in situ and/or in vivo electrical characteristics of the implanted electrodes, and the like. Accordingly, it becomes desirable to accurately characterize the electrical loads or impedances presented by the IPG lead system under in situ and/or in vivo conditions such that a particular therapy setting may be dynamically modified, modulated, or otherwise adjusted to an optimized setting based on the real-time parameterization of the electrical loads modeled by an equivalent ETI circuit arrangement as set forth above. Further, it is also advantageous to obtain an IPG's electrical load information in real-time without unduly interfering with a normal stimulation program or protocol implemented for an individual patient therapy application as well as without incurring extra cost in terms of processing, battery power, etc.

Embodiments set forth herein advantageously utilize a ramping process or sequence for the stimulation parameters (e.g., stimulation current pulse width, current amplitude, pulse repetition frequency, etc.) when therapy is initially turned on for the patient, and/or in some cases, when therapy is deactivated, for obtaining real-time in vivo voltage measurements relative to the stimulated electrodes optionally using one or more Kelvin connection paths, which may be used for characterizing an electrode-tissue interface associated with an implanted lead system. In general, such ramp-up and/or ramp-down sequences may typically be implemented to alleviate unpleasant "shocking" sensations for the patient, and example embodiments may be configured to leverage such ramping sequences for capturing induced voltage relationships under different ramp settings, which may be analyzed for extracting ETI parametric data.

Figure 2A:
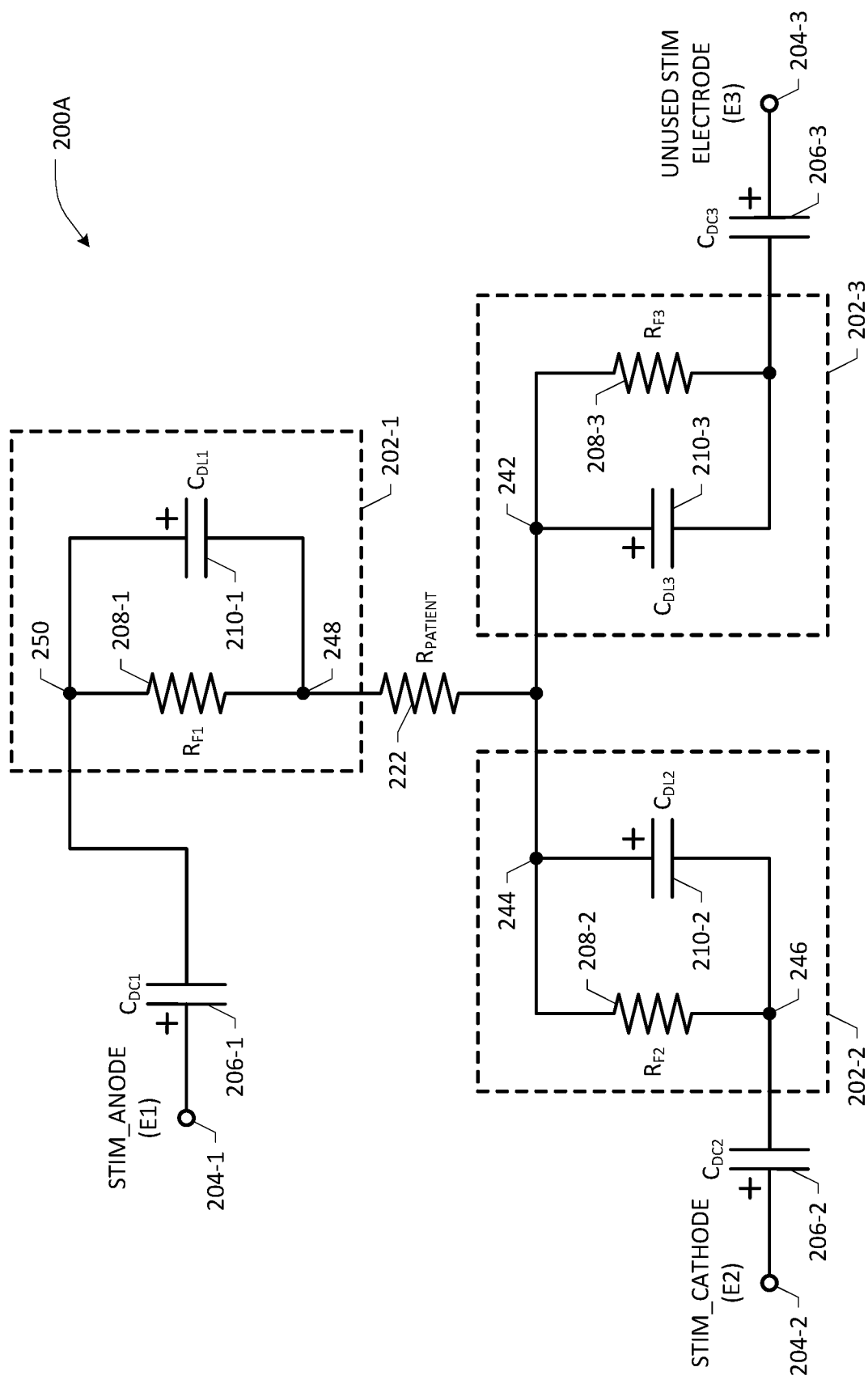
FIG. 2A depicts an example equivalent ETI circuit diagram for facilitating electrode voltage measurements in a sample electrode system using one type of Kelvin connection path according to an embodiment of the present disclosure.

FIG. 2A depicts an example equivalent circuit diagram 200A configured for facilitating electrode voltage measurements in a sample electrode system using one type of Kelvin connection path for purposes of an embodiment of the present disclosure. Three electrodes (E1, E2 and E3) and respective tissue interfaces 202-1 to 202-3 are shown by way of example. Illustratively, electrodes E1 and E2 are configured as stimulation anode and cathode, respectively, with electrode E3 being left unused or inactive. Each electrode is provided with a respective DC blocking stimulation capacitor $C_{DC}$, which facilitates a terminal or node with respect to an interface block coupled to suitable diagnostic/sense circuitry as described previously. Further, each ETI 202-1 to 202-3 is exemplified by a corresponding $C_{DL}$ 210-1 to 210-3 coupled in parallel to respective charge transfer resistance $R_F$ 208-1 to 208-3, that is in series connection with the bulk patient resistance $R_{PATIENT}$ 222 effectively disposed between a pair of the electrodes in any applicable combination. Because E3 is configured as an unused electrode for stimulation, its DC blocking stimulation capacitor $C_{DC3}$ 206-3 is kept in a discharged state, which allows the associated terminal 204-3 to be used in a Kelvin connection path with respect to other electrode terminals in a measurement circuit loop. For example, a measurement loop between terminal 204-2 of cathode-active electrode E2 and terminal 204-3 of unused electrode E3 can be used to measure a voltage comprising a sum of a voltage across $C_{DC2}$ 206-2 and a voltage across $C_{DL2}$ 210-2 because terminal 204-3 is at the same level as internal nodes 242 and 244 of the circuit arrangement 200A. In a typical DBS implementation where CDC capacitances are substantially larger than the $C_{DL}$ capacitances (e.g., by one or more orders of magnitude), the charge buildup on the DC blocking stimulation capacitors may be small enough that it may be ignored in estimating the voltage measurement across $C_{DL}$ associated with the selected active electrode, e.g., E2. In such a scenario, the voltage measurement may therefore be treated as being sufficiently close to the voltage component due to the buildup associated with $C_{DL2}$ 210-2. On the other hand, in typical SCS implementations, the differences between $C_{DL}$ and CDC capacitances are usually less than one order of magnitude (e.g., around seven times). Accordingly, in such an application, the charge buildup on SCS DC blocking stimulation capacitors ($C_{DC}$) cannot be ignored for voltage measurements as readily.

In similar fashion, a voltage measurement loop between terminal 204-1 of electrode E1 (configured as an anode stimulation node) and terminal 204-3 of unused electrode E3 can be effectuated in order obtain an induced voltage measurement at a particular stimulation setting. Such a voltage may include a component representing voltage buildup across $C_{DC1}$ 206-1 and voltage buildup across $C_{DL1}$ 210-1 since terminal 204-3 is at the same voltage level as internal nodes 242 and 248 (because outside of stimulation there is little current flow in the inactive electrode path through the bulk tissue resistance $R_{PATIENT}$ 222; however, the inactive electrode is most generally used as a Kelvin connection only when there is no stimulation nor discharge current flowing through the patient/tissue, although there can be exceptions). Further, the induced voltage measurement may be treated as a reasonable approximation of the voltage buildup after stimulation across $C_{DL1}$ m, 210-1 since $C_{DC1}$ 206-1 is typically much larger than $C_{DL1}$ 210-1 in certain applications, as noted previously. An example implementation of the circuit arrangement 200A may comprise CDC capacitances around 20-30 µF whereas the $C_{DL}$ capacitances may be around 0.1-3.0 µF. Skilled artisans will also recognize that the CDC capacitance values may be even lower, e.g., around 10-15 µF, especially in smaller physical form factor implementations. Where the $C_{DC}$ capacitance cannot be ignored, however, an equivalent capacitance ($C_{EQ}$) comprising the series combination of the CDC capacitance and the $C_{DL}$ capacitance in the Kelvin voltage measurement path may be characterized, wherein $1/C_{EQ}=1/C_{DC}+1/C_{DL}$, from a voltage-time functional relationship as will be set forth below.

Accordingly, a Kelvin connection path effectuated via the $C_{DC}$ terminal of an inactive electrode of an implantable lead system may be used for obtaining an induced voltage measurement associated with any of the active electrodes of the lead system that are stimulated at a particular stimulation setting during a ramping up sequence or a ramping down sequence, wherein an added voltage component associated with the $C_{DC}$ capacitor corresponding to the selected active electrode is included in the voltage measurement. To separate this additional voltage component from the measurement path, an AC-coupling sense capacitor path of an active electrode may be used in example embodiments as a Kelvin connection path at the other end of the measurement loop in conjunction with a Kelvin connection path at an inactive electrode as set forth above. In further embodiments, an inactive electrode may also be provided with an AC-coupling sense capacitor path (which is a likely implementation scenario since it is preferable to manufacture identical electrodes in a lead system that can be selectively and dynamically configured depending on a particular stimulation application and associated stimset variations). In such embodiments, an alternative Kelvin connection path may be established at the inactive electrode in addition to the inactive DC blocking stimulation $C_{DC}$ capacitor path thereat. One skilled in the art will therefore readily appreciate that a number of Kelvin connection modes may be effectuated in an example IMD/IPG system depending on the various AC-coupling and/or DC blocking stimulation capacitor arrangements provided with respect to the electrodes of a lead system and/or how the different electrodes and corresponding capacitor arrangements are selectively configured. For example, where a subset of the electrodes are configured to be active, the remaining electrodes (one or more of the rest of the electrodes) may be disposed as inactive electrodes, out of which any one particular electrode may be configured as one end of a Kelvin connection path with respect to a voltage measurement loop. Such a Kelvin connection path may be effectuated via the selected inactive node's DC blocking stimulation capacitor path or via its AC-coupling sense capacitor path, as noted above. In an additional/alternative embodiment, one of the electrodes of a lead system may be designated or dedicated to operate as a Kelvin connection terminal for effectuating in vivo voltage measurements with respect to any one of the active electrodes of the lead system for purposes of the present patent disclosure.

Figure 2B:
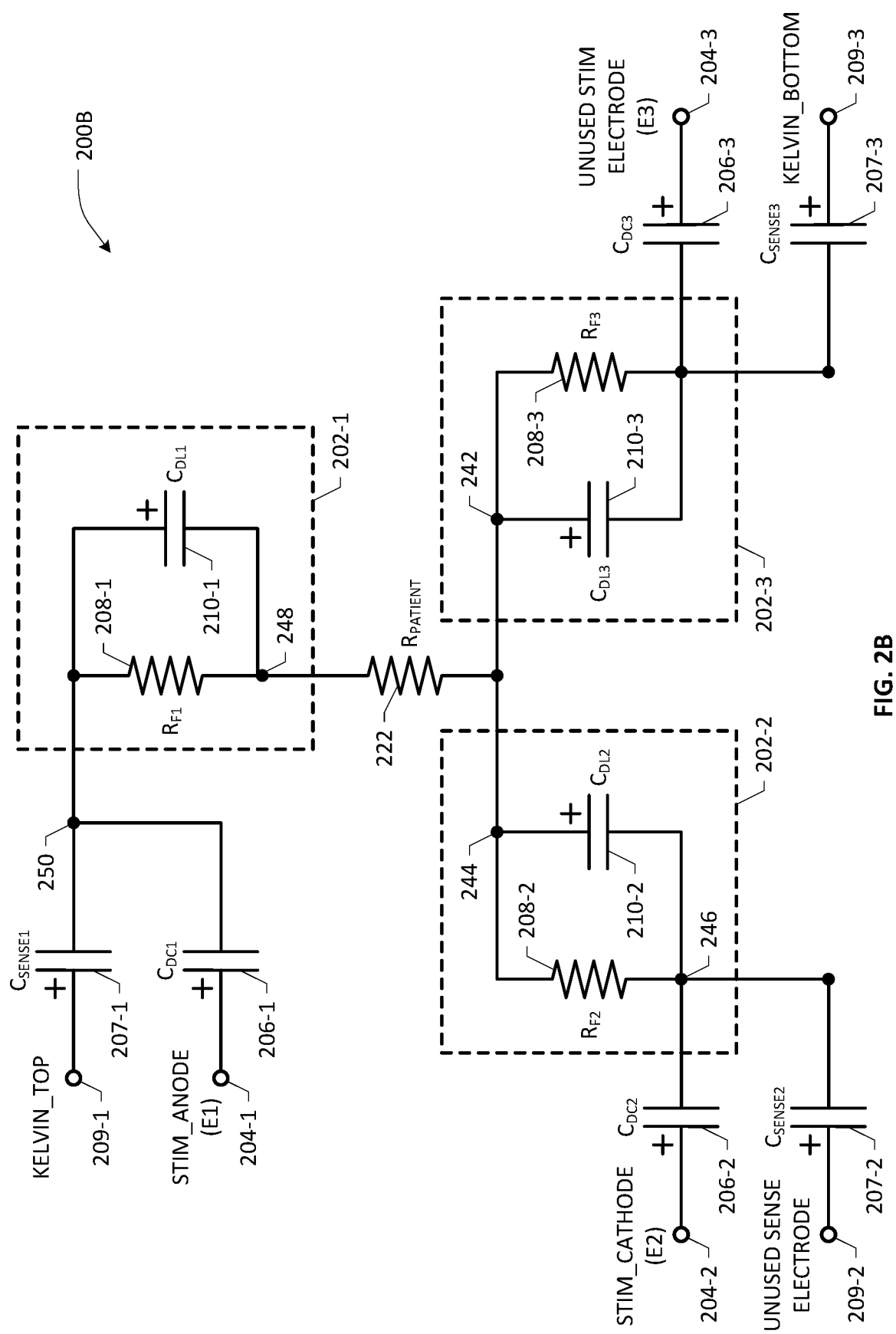
FIG. 2B depicts an example equivalent ETI circuit diagram for facilitating electrode voltage measurements a sample electrode system using a combination of Kelvin connection paths according to another embodiment of the present disclosure.

Turning to FIG. 2B, depicted therein is an example equivalent ETI circuit diagram 200B configured to exemplify one or more of the foregoing embodiments for facilitating in vivo voltage measurements during a ramp-up or ramp-down sequence of stimulation using different types and/or combinations of Kelvin connection paths according to the present patent disclosure. Similar to the arrangement 200A illustrated in FIG. 2A, circuit arrangement 200B of FIG. 2B exemplifies three electrodes, E1-E3, each shown with corresponding ETI circuit representations 202-1 to 202-3 coupled to bulk patient resistance $R_{PATIENT}$ 222 in a "star" configuration. Further, electrodes E1 and E2 are illustrated as active stimulation nodes while electrode E3 is left as an inactive/unused electrode as before. Each electrode is provided with corresponding biosensing input terminal 209-1 to 209-3, effectuated via respective AC-coupling capacitors $C_{SENSE1}$ 207-1 to $C_{SENSE3}$ 207-3 that are coupled in parallel to the respective $C_{DC1}$ 206-1 to $CDCl_3$ 206-3 capacitors. In one embodiment, the AC-coupling capacitors $C_{SENSE1}$ 207-1 to $C_{SENSE3}$ 207-3 may be implemented as low capacitance components (e.g., around 0.1 µF), which may be maintained to be readily kept in a discharged state (e.g., because no stimulation current will flow through such capacitors). Accordingly, voltage levels at the AC-coupling capacitors $C_{SENSE1}$ 207-1 to $C_{SENSE3}$ 207-3 of electrodes E1-E3 are near or close to 0 V (or some other reference potential), which can facilitate respective Kelvin connection paths for measuring the induced electrode voltages in connection with a select voltage measurement loop depending on which electrode's voltage is being measured. For example, $C_{SENSE1}$ 207-1 terminal 209-1 may be deemed a "Kelvin_Top" terminal or node which is at the same potential as internal node 250 with respect to ETI 202-1 of electrode E1. By utilizing $C_{SENSE3}$ 207-3 terminal 209-3 of the unused electrode E3 as a "Kelvin_Bottom" terminal (which is at the same potential as internal node 242), an induced voltage measurement across $C_{DL1}$ 210-1 after stimulation at a particular setting may be obtained in a manner similar to the voltage measurement process discussed above. Further, the $C_{DC3}$ terminal 204-3 of the unused electrode E3 may also be used in conjunction with the $C_{SENSE1}$ 207-1 terminal 209-1 operating as the "Kelvin_Top" terminal in an alternative embodiment, as previously described. Skilled artisans will recognize this alternative Kelvin connection path may be beneficial to use if the biosensing AC-coupling $C_{SENSE3}$ 207-3 terminal 209-3 associated with electrode E3 is already in use for biosensing and it is required that the sensing activity from electrode E3 remain undisturbed. Likewise, voltage buildup at other active electrodes (i.e., across respective $C_{DL}$ capacitances) may be measured after stimulation by using corresponding $C_{SENSE}$ terminal inputs in conjunction with either of the Kelvin connection paths available at the unused electrode E3 in a similar manner.

In one example scenario, if voltage measurements are taken using a Kelvin connection path between node 209-1 and node 204-3 or node 209-3, $C_{DC1}$ 206-1 is not in the series combination with $C_{DL1}$ 210-1, and hence only the double-layer capacitance of the equivalent ETI circuit of E1 electrode may be characterized. On the other hand, if node 204-1 of the DC capacitance associated with E1 electrode is utilized for taking voltage measurements with respect to either node 204-3 or node 209-3, $C_{DC1}$ 206-1 is included in a series combination with $C_{DL1}$ 210-1, and hence an equivalent $C_{EQ1}$ capacitance associated with E1 electrode may be characterized based on the voltage measurements as will be set forth below. Likewise, different Kelvin connection paths involving electrical nodes associated with cathodic E2 electrode and electrical nodes associated with the unused E3 electrode may be used for voltage measurements for characterizing $CDCl_2$ 206-2, $C_{DL2}$ 206-2, and/or $C_{EQ2}$ capacitances in addition to the resistive components of the ETI circuit arrangement associated with E2 electrode.

Whereas example Kelvin connection paths illustrated above involve a pair of electrodes across the EPI/ETI interface with suitable capacitor terminals operating as Kelvin connection terminals, additional and/or alternative embodiments according to the teachings of the present invention may also involve any combination of any subset of the active electrodes and any subset of the unused/inactive electrodes in a Kelvin connection path on the either side of the EPI interface for obtaining voltage measurements at different stimulation settings in a ramp-up and/or ramp-down sequence, with appropriate capacitor terminal connections as described herein, mutatis mutandis, for obtaining in vivo electrical load characterizations of different portions of an IPG lead system. Additional details regarding implementing Kelvin connections in an IPG and associated lead systems comprising one or more leads may be found in U.S. patent application Ser. No. 16/195,502, filed Nov. 19, 2018, entitled, "KELVIN CONNECTION SCHEME FOR DIAGNOSTIC CAPABILITY IN A NEUROSTIMULATOR", hereinafter "the Kelvin Connection patent application", which is incorporated by reference herein.

Electrode voltage measurements obtained in vivo using a Kelvin connection scheme as set above at different stimulation settings may be used for characterizing the respective equivalent ETI circuit representations thereof for purposes of the present patent disclosure, wherein the bioimpedance parameters $R_S$, $R_F$, $C_{DL}$, $C_{DC}$ or $C_{EQ}$ of the equivalent circuit loads may be extracted according to example embodiments herein. For example, in an illustrative scenario, for a target stimulation setting comprising a constant current pulse of 10 mA having a pulse width 200 µs, a ramping sequence may involve varying the amplitude, the pulse width and/or both in different combinations until the target stimulation setting is reached and energizing a select one or more electrodes configured for stimulation therapy at each combination. A series of diagnostic voltage measurements may be obtained by the IMD/IPG (e.g., using one or more ADC converters of the diagnostic/sensing circuitry) from the stimulation electrodes and/or Kelvin connection sense terminals, or inactive electrodes of the lead system at each setting combination. A non-limiting example ramp-up sequence is illustrated below:

TABLE 1

| Step | I, mA | Pulse Width, µs |
|---|---|---|
| 1 | 2 | 40 |
| 2 | 2 | 50 |
| 3 | 4 | 50 |
| 4 | 4 | 60 |
| 5 | 6 | 60 |
| 6 | 6 | 75 |
| 7 | 8 | 75 |

TABLE 1-continued

| Step | I, mA | Pulse Width, µs |
|---|---|---|
| 8 | 8 | 100 |
| 9 | 10 | 100 |
| 10 | 10 | 120 |
| ... | ... | ... |
| N | 10 | 200 |

In some example embodiments, the voltage measurements may be recorded, processed, and/or further analyzed, using a variety of techniques, either within the IPG/IMD, in association with an external device, or at a remote data analytics platform, or in any combination, so that electrical load parametric values can be extracted in an actual real-time in situ application, which may provide useful information about the ETI, the entire IPG load, and/or about the integrity of the stimulation leads/electrodes. Use of such information may also make it possible to ascertain therapy effectiveness, improve therapy efficiency (e.g., thereby improving IPG battery longevity), etc. Further, such electrical load parametric information may be used to monitor shifts in the tissue characteristics of the patient in order to identify any abnormalities.

Example embodiments herein take advantage of the fact that the induced voltages at the IPG electrodes during a constant current stimulation pulse are dependent upon three components: (i) the stimulation setting parameters (e.g., the current amplitude, pulse width, etc.); (ii) the electrical/bioimpedance parameters of the load network over which the IPG is delivering the constant current stimulation pulse; and (iii) any residual charge that might have been present on the capacitors in the IPG load network from prior stimulation delivery. Details regarding the effect of residual voltages on the electrode voltage characteristics in an IPG system may be found in the Kelvin Connection patent application, incorporated by reference hereinabove. In the context of the present patent application, a residual voltage merely moves the baseline of an induced voltage functional relationship by a constant amount over the pulse width regardless of the amplitude and as such may be factored out in a bioimpedance parametric characterization scheme without loss of generality.

In some embodiments, electrode voltage measurement data may be analyzed using regression techniques, numerical/analytical approximations, as well as "trial and error" methods using circuit simulation/modeling techniques (e.g., SPICE), and the like, to obtain parametric values corresponding to $R_S$, $R_F$, $C_{DL}$, $C_{DC}$ or $C_{EQ}$ of the equivalent ETI circuit loads. Whereas some of the bioimpedance parameters show linear dependencies, others may exhibit nonlinear relationships because of higher-order dependencies on the stimulation current parameters, charge state, current density, etc. Some example embodiments may therefore employ a "guess-and-iterate" approach using transcendental equations, i.e., equations that do not have closed-form solutions and comprise one or more transcendental functions (analytical functions that do not satisfy a polynomial equation, in contrast to algebraic functions). As an illustration, the Faradaic resistance component ($R_F$) of an equivalent circuit corresponding to an electrode may be extracted in some embodiments based on an exponentially decaying capacitor current that flows through the $C_{DL}$ component of the equivalent circuit.

Additional and/or alternative embodiments may involve performing a waveform analysis that employs closed-form equations for approximating different portions of a voltage-time functional relationship over sufficiently close points in time. Skilled artisans will recognize that such embodiments are particularly advantageous in some implementations because the closed-form techniques are computationally efficient in general, as they do not require iterative computations or complicated mathematical analysis. Additionally, example waveform-based analytical methods allow for the estimation of the $R_F$ Faradaic resistance component at multiple points in time, which may be used for obtaining a more accurate assessment of the ETI parametric information.

Figure 3:
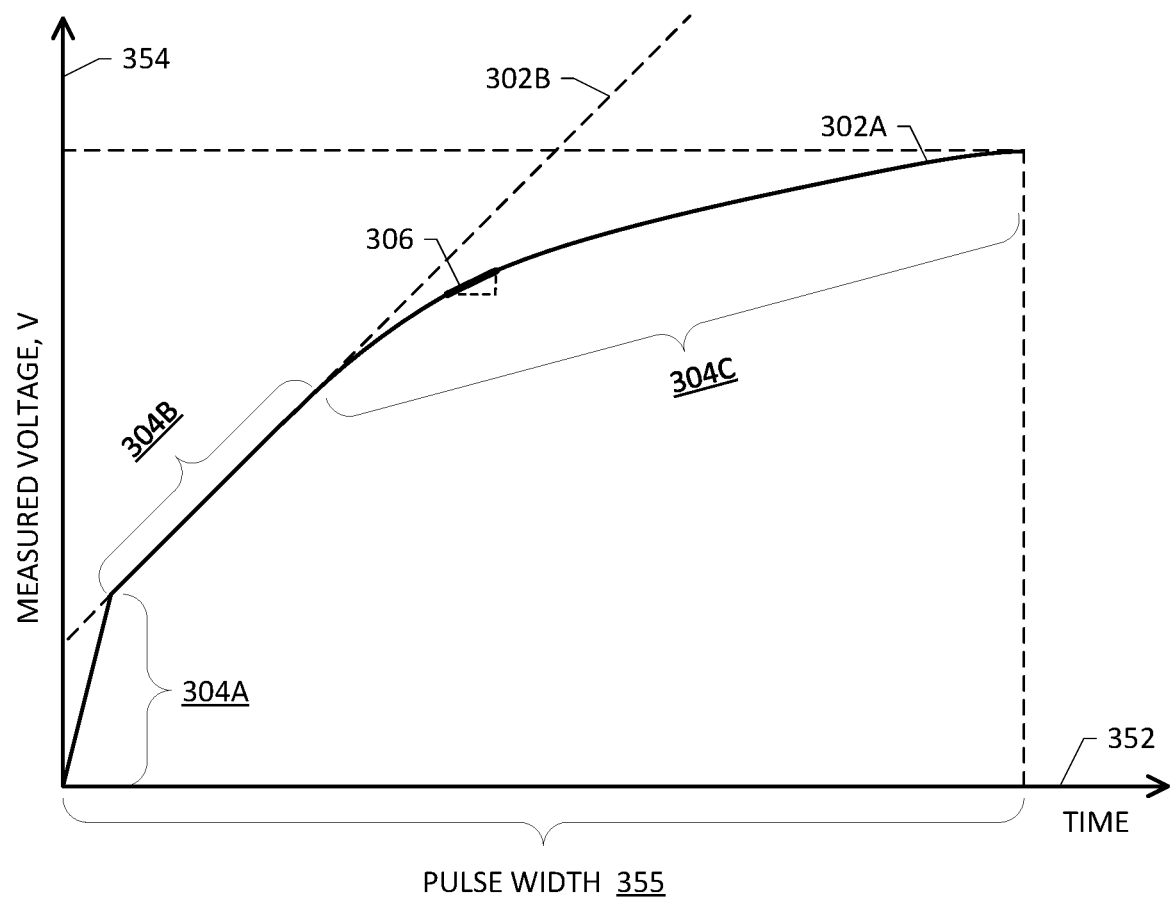
FIG. 3 depicts a voltage-time functional relationship based on voltage measurements obtained with respect to a stimulated electrode during a ramping up sequence or a ramping down sequence of a stimulation therapy.

FIG. 3 depicts an example voltage-time functional relationship with respect to a stimulated electrode based on voltage measurements obtained at a particular stimulation setting for a constant current pulse (e.g., a given amplitude and a pulse width) during a ramp-up sequence or a ramp-down sequence of a stimulation therapy. As noted previously, because a residual voltage merely moves the baseline of an induced voltage functional relationship by a constant amount, any pre-stimulation residual voltage present on the stimulated electrode may be factored out mathematically. Accordingly, for example, it should be appreciated that the embodiment depicted in FIG. 3 illustrates voltage measurements which already have subtracted from the data any residual offset voltage on the electrode (i.e., from prior stimulation events) measured immediately prior to delivery of the stimulation pulse during therapy. Voltage measurements taken at different times during a constant current amplitude stimulation pulse having a pulse width 355 may be plotted on Y-axis 354 as a curvilinear function 302A of time, represented on X-axis 352. A straight line 302B is representative of a slope voltage waveform that may be fitted to at least a portion of the curvilinear function 302A. Voltage functional relationship curve 302A may include a substantially step-wise function portion 304A (which in a voltage measurement waveform 302B comprises the Y-intercept indicating the transient voltage increase when the instantaneous current is flowing through the bulk resistance, $R_S$, after having removed from the measurement data any residual voltage from previous stimulation pulses). This voltage may be measured immediately after the current pulse is applied. However, due to the practical nature of measurements, this portion of the Voltage functional relationship curve 302A may show a linear relationship having a very steep slope (e.g., a substantially step-wise relationship with time). Portion 304A is followed by a linear functional portion 304B, which is then followed by a non-linear functional portion 304C that eventually reaches an asymptotic value as the current over the pulse width 355 is applied.

An example waveform analysis of a voltage-time functional relationship may involve one or more assumptions depending on the implementation in order to simplify the parametric characterization analysis. For example, some embodiments may ignore a select initial time period during the pulse width, which is due to analog rise time of the current pulse. In some embodiments, voltage-time relationship plots or graphs may be constructed for each current amplitude and/or pulse width, with voltages measured on the way to the target amplitude setting. In still further embodiments, the series combination capacitance ($C_{EQ}$) of an equivalent ETI circuit may be assumed to remain unchanged during at least a portion of the pulse duration. It should be appreciated however that not all such assumptions are required in an example embodiment.

In one example embodiment, the series combination capacitance ($C_{EQ}$) (or $C_{DL}$ where no DC-coupling capacitors $C_{DC}$ are provided) of an equivalent ETI circuit may be extracted using the slope of the measured voltage waveform over a configurable time duration starting at $T_1$ and ending at $T_2$, which may comprise a portion of the linear functional region 304B of the measured voltage waveform. Where $V_1$ and $V_2$ are the measured voltages at $T_1$ and $T_2$, respectively, I is the programmed current amplitude, $C_{EQ}$ may be determined from the following expression:

$$C_{EQ} = [I*(T_2-T_1)]/(V_2-V_1)$$

In one example embodiment, the bulk/patient resistance ($R_S$), may be determined based on the $C_{EQ}$ (or $C_{DL}$) value determined above and a voltage measurement taken at the end of the initial analog rise time. Since the voltage value at $T_0 = 0$ μs is not practically measurable, the pure resistive component can be estimated based on the extrapolation of the straight line equation y=mx+b for the constant slope line (e.g., line 302B), using the slope (m) and the known rise time period (τ) to obtain the Y-intercept. With $V_1$ being the voltage measured at the end of the rise time (τ), $V_0$ can be calculated as follows:

$$V_0 = V_1 - (m*\tau).$$

Because of Ohm's law, R=V/I, the bulk/patient resistance ($R_S$) is determined as:

$R_S = V_0/I$, where I is the programmed current amplitude.

It should be noted that the computed resistance, $R_S$, includes no resistive contribution from any of the RF elements in the ETI, since the capacitances ($C_{EQ}$, $C_{DC}$, and $C_{DL}$) will not allow nearly instantaneous changes to build-up across the ETI other that that which $R_S$ alone will allow.

With respect to estimating the Faradaic resistance, $R_F$, whose effect is seen in the nonlinear portion of a voltage-time relationship, e.g., portion 304C illustrated in FIG. 3, a piecewise portion 306 thereof for a sufficiently small time period may be assumed to be linear. In an example scenario where $C_{EQ}$ (or $C_{DL}$) is not changing during a pulse, the slope dV/dT would be constant for any given current amplitude, as illustrated by the constant slope line 302B in FIG. 3. With the total delivered stimulation current and $C_{EQ}$ (or $C_{DL}$) treated as constant during a stimulation pulse, the only electrical variable changing during the pulse would be the portion of the current charging the capacitance, which can be $C_{EQ}$ or $C_{DL}$. The remaining current is flowing through the Faradaic resistance ($R_F$) which bypasses the double-layer capacitance, thereby asymptotically reducing the slope observed in the measured voltage waveform. Accordingly, for a short time duration (preferably, 1-10 μs for pulse widths which typically are of appreciably longer duration), the measured slope dV/dT may be used to estimate the current flowing through the capacitive component, which allows estimation of the current through the Faradaic resistance (because total stimulation current=current through the capacitive component+current through the Faradaic resistance, due to conservation of charge and current). Once the current through the Faradaic resistance is estimated, the $R_F$ value may be determined in accordance with Ohm's law.

In an example implementation of the foregoing $R_F$ characterization scheme, the following may be utilized:

dV/dT=Voltage vs. time slope near the end of the pulse (smaller dT leads to more accurate estimates.)
$C_{EQ}$=Equivalent capacitance estimated as above
$I_1$=Programmed current amplitude
$V_0$=0 μs voltage calculated as above
$T_2$=Second time point used in finding dV/dT
$I_2$=Current flowing through capacitance (not bypassed by $R_F$)
$I_{RF}$=Current through Faradaic Resistance Current ($I_2$) flowing through capacitance may be determined as follows:

$$I_2 = C_{EQ}*(dV/dT)$$

Accordingly, $I_{RF}$ may be estimated as ($I_1-I_2$). Applying Ohm's law gives the Faradaic resistance as follows:

$$R_F = (V(T_2)-V_0)/I_{RF}$$

In further embodiments, parametric data obtained from the voltage-time relationships for each amplitude setting may be used obtain functional relationships between the individual electrical load parameters of the ETI circuit and the amplitude to determine current density dependence. Likewise, additional functional relationships between the load parameters and other stimulation parameters may also be obtained for purposes of some embodiments of the present patent disclosure.

Figure 4A:
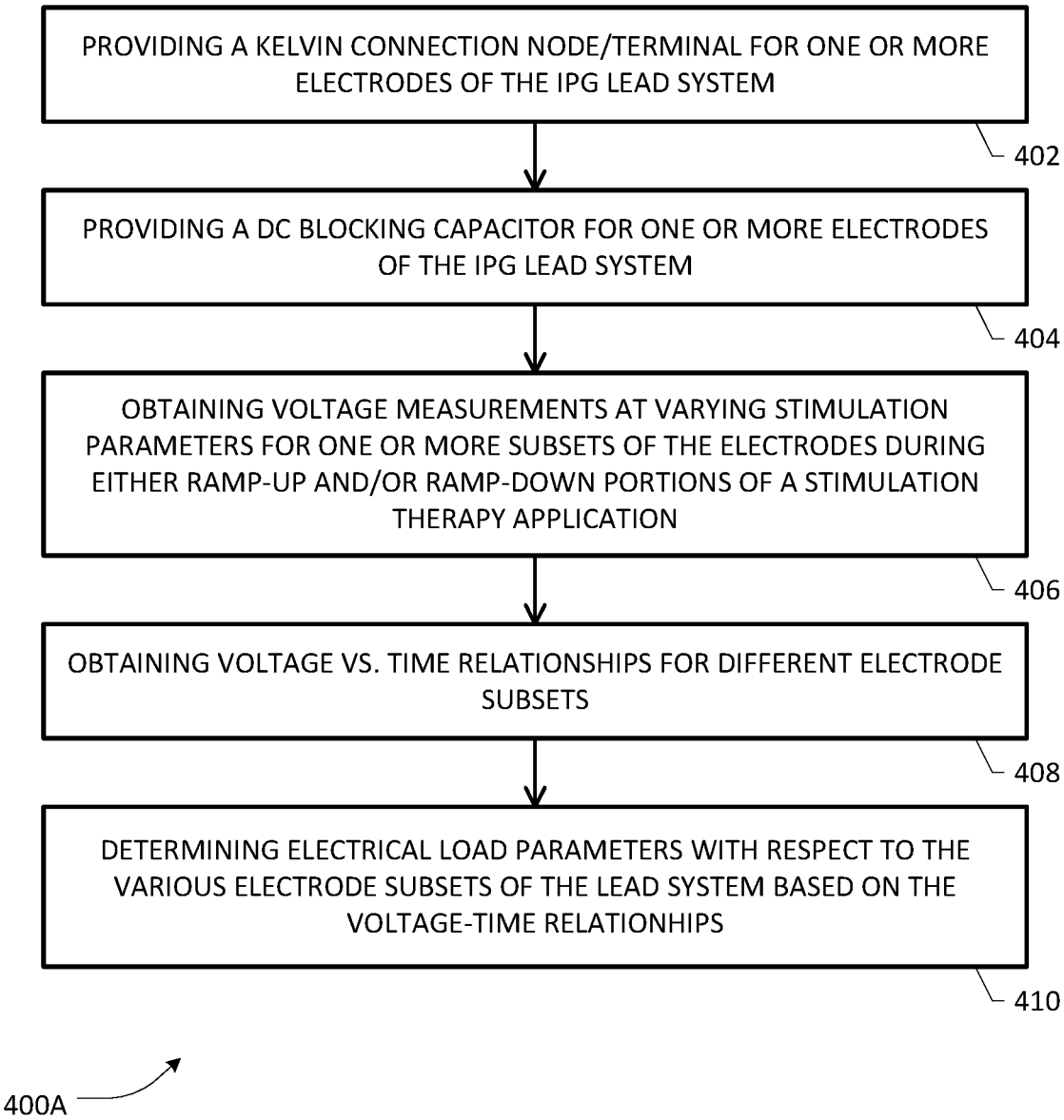
FIGS. 4A-4C depict flowcharts illustrative of blocks, steps and/or acts that may be (re)combined in one or more arrangements with or without other flowcharts regarding ETI electrical load parametric characterization of an IPG/IMD lead system according to some embodiments of the present disclosure.
Figure 4B:
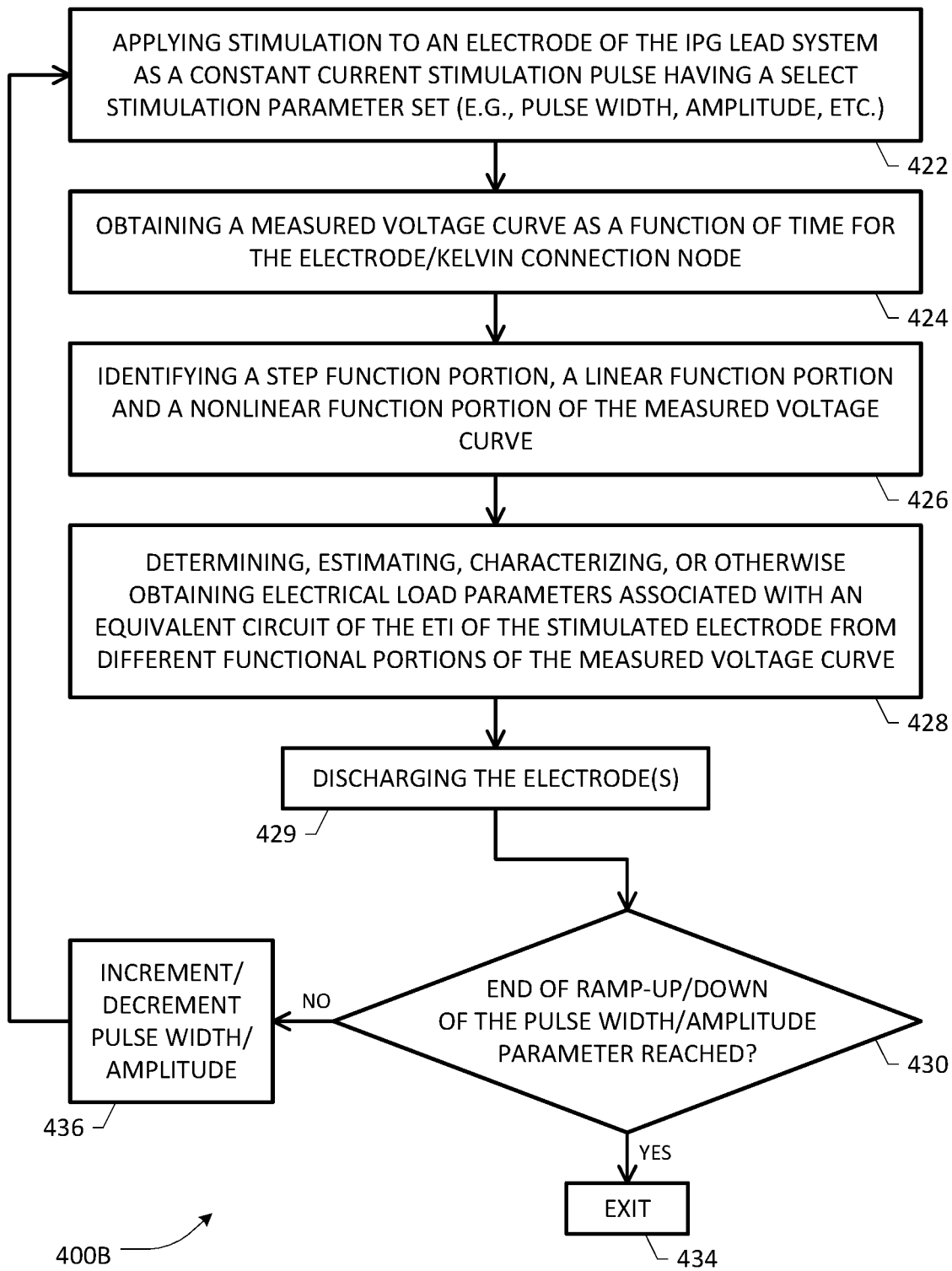
Figure 4C:
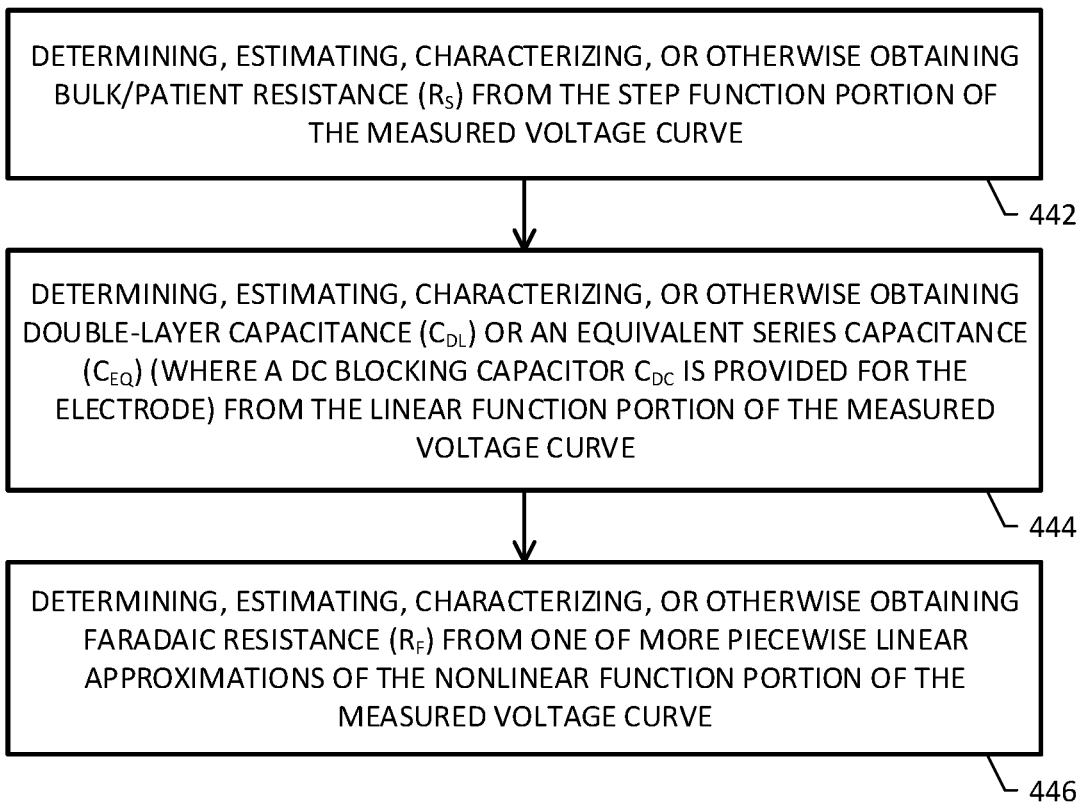

FIGS. 4A-4C depict flowcharts illustrative of blocks, steps and/or acts that may be (re)combined in one or more arrangements with or without other flowcharts of the present disclosure regarding ETI electrical load parametric characterization of an IPG/IMD lead system according to some embodiments of the invention. In one embodiment, example process 400A of FIG. 4A may involve providing a Kelvin connection node/terminal for one or more electrodes of the lead system, e.g., by coupling respective AC-coupling capacitors ($C_{SENSE}$) as set forth hereinabove (block 402). At block 404, DC blocking capacitors ($C_{DC}$) may be provided for one or more electrodes of the lead system. As described previously, one or more inactive electrodes as well as dedicated Kelvin electrodes may also be provided in an IPG lead system for purposes of facilitating in vivo voltage measurements a variety of connection paths using different combinations of the electrical nodes associated with the electrodes. At block 406, voltage measurements may be obtained at varying stimulation parameters for one or more electrodes during at least one of a ramping up sequence or a ramping down sequence of a stimulation therapy application. At block 408, voltage vs. time relationships for different electrodes or electrode subsets may be obtained. At block 410, one or more electrical load parameters of equivalent ETI circuit arrangements with respect to the various electrodes or subsets may be obtained based on the voltage-time relationships as set forth above.

Example process 400B depicted in FIG. 4B sets forth operations that may be performed in relation to a ramp-up or ramp-down sequence of a therapy application. At block 422, stimulation may be applied to an electrode (or its Kelvin connection node) of the IPG lead system as a constant current stimulation pulse having a select stimulation parameter set (e.g., pulse width, amplitude, etc.). At block 424, a measured voltage curve may be obtained as a function of time for the electrode/Kelvin connection node. At block 426, a step function portion, a linear function portion and a nonlinear function portion of the measured voltage curve may be obtained as set forth above with respect to FIG. 3. At block 428, various electrical load parameters associated with an equivalent circuit of the ETI of the stimulated electrode may be determined, estimated, extracted or otherwise obtained from different functional portions of the measured voltage curve. In an example therapy scenario, discharge of the stimulation electrodes may be effectuated after each stimulation pulse, i.e., before the stimulation parameters are ramped up or down, as set forth at block 429. A determination may be made whether the ramp-up or ramp-down sequence with respect to the select stimulation parameter (e.g., pulse width, amplitude, etc.) has reached a termination (block 430). In a ramp-up therapy sequence, the termination may signify stimulating the electrodes at a target stimulation setting. In a ramp-down therapy sequence, the termination may signify deactivating the electrodes initially energized at a particular preconfigured therapy setting. Upon reaching either the ramp-up or ramp-down sequence termination, the process flow exits (block 434). Otherwise, the select stimulation parameters may be incremented and/or decremented accordingly (block 436) and stimulation may be applied to the electrodes for further voltage measurements.

With respect to an example waveform analysis of a measured voltage-time functional relationship, example process 400C of FIG. 4C may be based responsive to identifying a substantially step-wise function portion, a linear function portion and a nonlinear function portion of the voltage-time functional relationship as previously noted. At block 442, a bulk patient resistance ($R_S$) of the equivalent ETI circuit associated with at least one electrode may be determined from the substantially step-wise function portion of the voltage-time functional relationship. At block 444, at least one of a double-layer capacitance ($C_{DL}$), a direct current (DC) blocking capacitance ($C_{DC}$), and an equivalent series capacitance ($C_{EQ}$) of the equivalent ETI circuit associated with the at least one electrode may be determined from the linear function portion of the voltage-time functional relationship. At block 446, a Faradaic resistance ($R_F$) of the equivalent ETI circuit associated with the at least one electrode may be determined from one or more piecewise linear approximations of the nonlinear function portion of the voltage-time functional relationship.

Figure 5A:
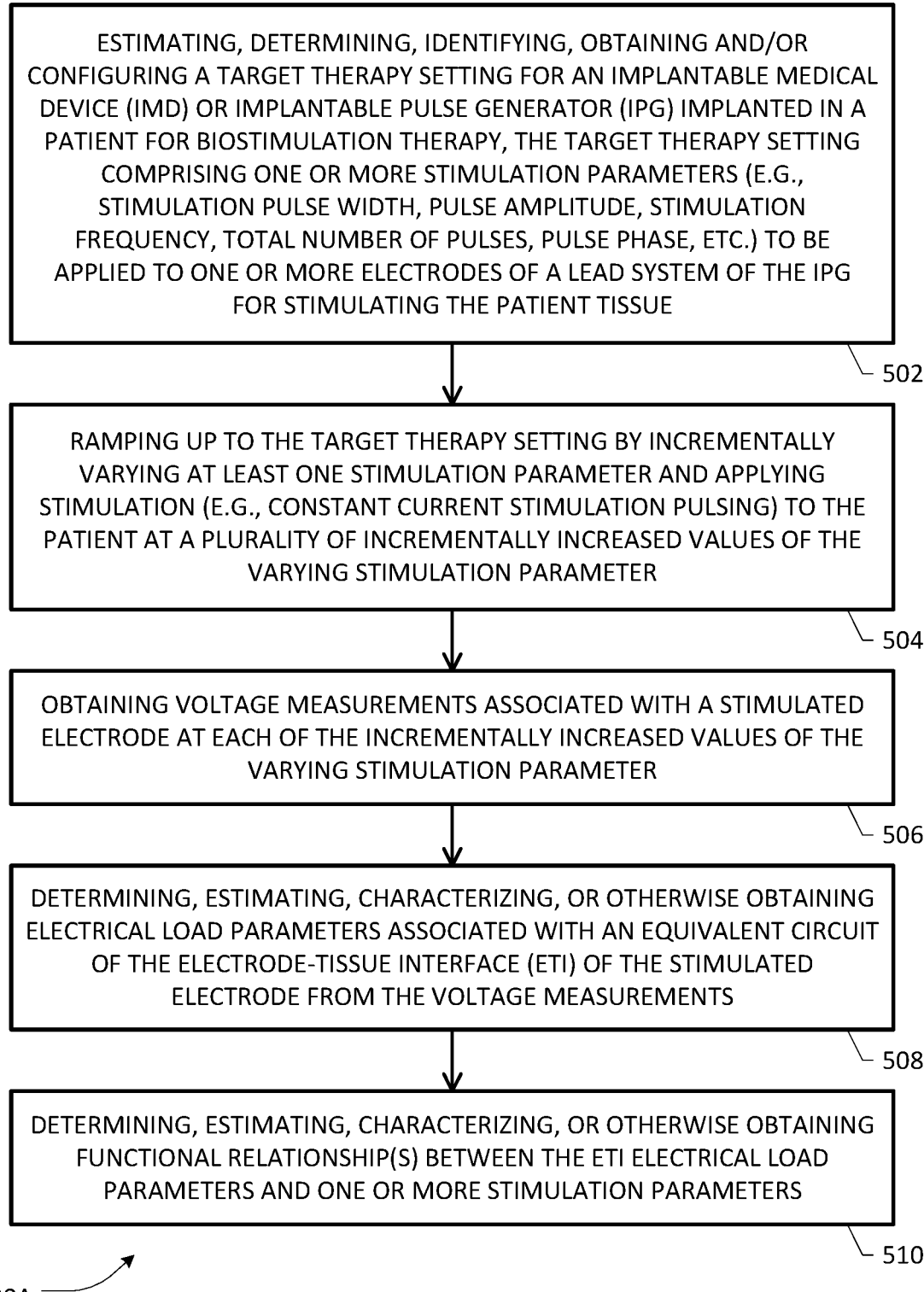
FIGS. 5A and 5B depict flowcharts illustrative of blocks, steps and/or acts that may be (re)combined in one or more arrangements with or without other flowcharts regarding ETI electrical load parametric characterization of an IPG/IMD lead system according to some embodiments of the present disclosure.
Figure 5B:
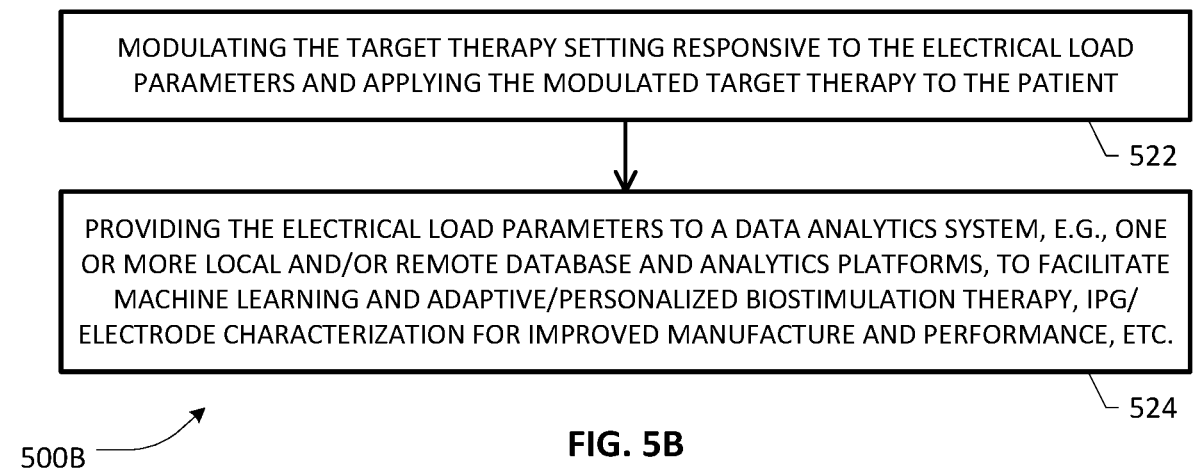

FIGS. 5A and 5B depict flowcharts illustrative of blocks, steps and/or acts that may be (re)combined in one or more arrangements with or without other flowcharts of the present disclosure regarding ETI electrical load parametric characterization of an IPG/IMD lead system according to some embodiments of the invention. Example process 500A sets forth various operations relating to in vivo parametric characterization during a ramp-up sequence, which may be based responsive to estimating, determining, identifying, obtaining and/or configuring a target therapy setting for an IMD/IPG implanted in a patient for biostimulation therapy (block 502). At noted previously, the target therapy setting may comprise one or more select stimulation parameters (e.g., stimulation pulse width, pulse amplitude, stimulation frequency, total number of pulses, pulse phase, etc.) to be applied to one or more electrodes of a lead system of the IPG for stimulating the patient tissue. At block 504, at least one stimulation parameter may be ramped up from an initial value by incrementally varying the stimulation parameter. Appropriate stimulation is applied (e.g., constant current stimulation pulsing) to the patient at a plurality of incrementally increased values of the varying stimulation parameter. At block 506, voltage measurements associated with a stimulated electrode at each of the incrementally increased values of the varying stimulation parameter are obtained. At block 508, various electrical load parameters associated with an equivalent circuit of the ETI of the stimulated electrode may be determined, estimated, characterized, or otherwise obtained from the voltage measurements based on a number of techniques as set forth previously. In a further aspect, process flow 500A may include determining, estimating, characterizing, or otherwise obtaining functional relationship(s) between the ETI electrical load parameters and one or more stimulation parameters (block 510).

Example process 500B of FIG. 5B sets forth operations that may be combined with other processes of the present patent disclosure. At block 522, the target therapy setting of a stimulation therapy may be modulated, adjusted or otherwise modified responsive to the electrical load parameters, whereupon the adjusted target therapy is applied to the patient for providing therapy until further reset. In additional embodiments, the electrical load parameters may be provided to a data analytics system, e.g., one or more local processing engines on the IPG/IMD, external programmer devices, and/or remote database and analytics platforms such as cloud-based datacenters, to facilitate data mining, machine learning, Big Data analytics, and adaptive/personalized biostimulation therapy, etc. Also, in still further embodiments, the electrical load parameters associated with IPG/electrode characterization may be provided to facilitate improved manufacture/fabrication of electrodes, optimized electrode performance, etc.

Figure 6:
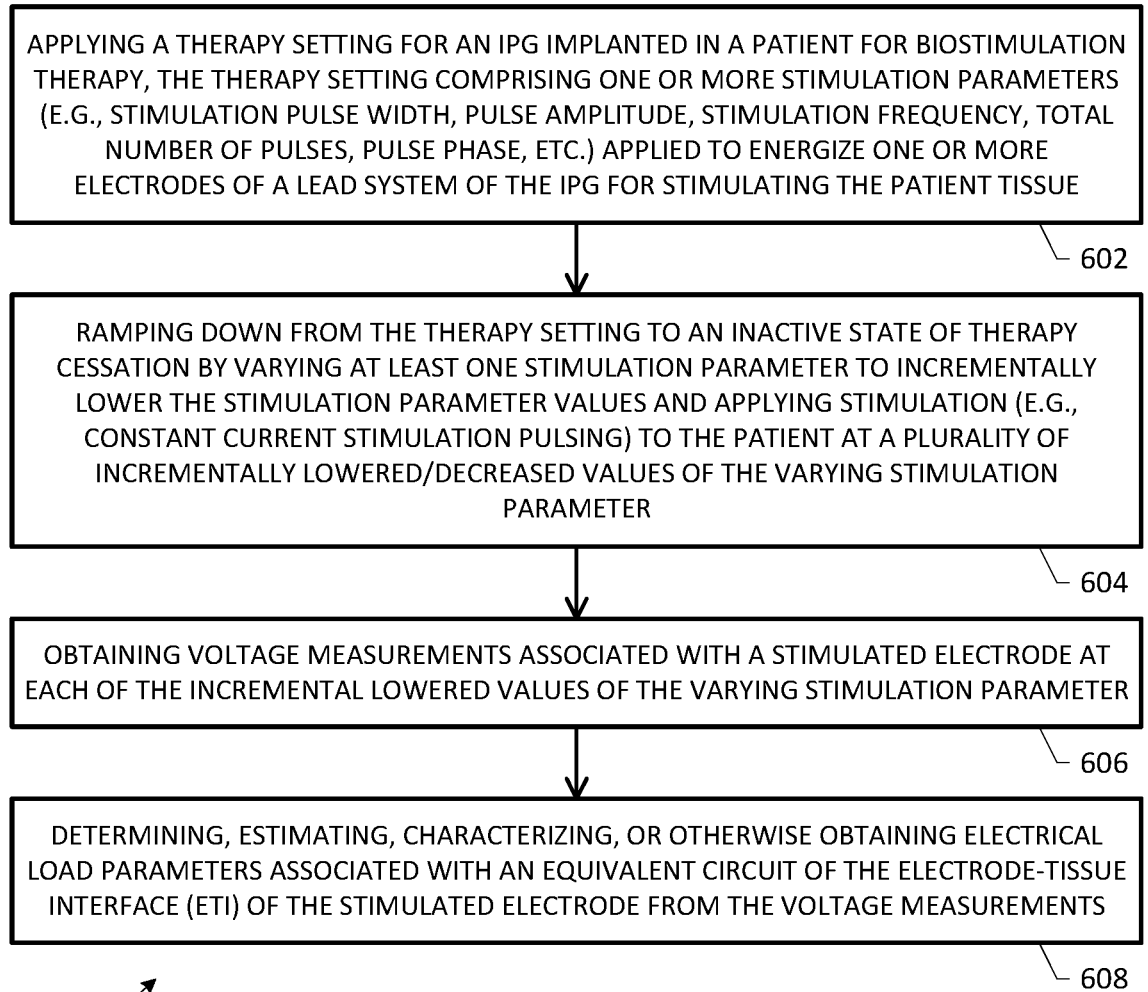
FIG. 6 depicts a flowchart illustrative of blocks, steps and/or acts that may be (re)combined in one or more arrangements with or without other flowcharts regarding ETI electrical load parametric characterization of an IPG/IMD lead system according to some embodiments of the present disclosure.

Example process 600 of FIG. 6 sets forth various operations relating to in vivo parametric characterization during a ramp-down sequence, which may be based responsive to applying a preconfigured therapy setting for an IMD/IPG implanted in a patient for biostimulation therapy (block 602). As noted previously, the therapy setting may comprise one or more select stimulation parameters of a constant current pulse stimulation (e.g., stimulation pulse width, pulse amplitude, stimulation frequency, total number of pulses, pulse phase, etc.) applied to energize one or more electrodes of a lead system of the IPG for stimulating the patient tissue. At block 604, the therapy may be ramped down to an inactive state of therapy cessation by varying at least one stimulation parameter to incrementally lower the stimulation parameter values. Stimulation may be applied to the patient (e.g., constant current stimulation pulsing) at a plurality of incrementally lowered/decreased values of the varying stimulation parameters (block 604). At block 606, voltage measurements associated with a stimulated electrode may be at each of the incremental lowered values of the varying stimulation parameter(s). At block 608, one or more electrical load parameters associated with an equivalent circuit of the ETI of the stimulated electrode from the voltage measurements using various techniques as set forth previously (block 608).

Skilled artisans will appreciate that example embodiments set forth herein may be implemented in various stimulation pulse delivery scenarios, e.g., using monophasic pulses, biphasic pulses, etc., for obtaining ETI load parametric data relative to one or more electrodes of an implanted stimulation lead system of an IPG. For example, a waveform analysis of measured voltage-time relationships could be performed for the reverse stimulation pulses of a biphasic pulse delivery scheme where appropriate ramp-up or ramp-down sequences may be employed in the reverse polarity regime, in a manner similar to the analysis set forth above relative to FIG. 3, mutatis mutandis, which exemplifies a measured voltage-time relationship obtained during the forward phase of a biphasic pulse or a monophasic pulse in the positive polarity regime. Further, where a biphasic pulse delivery scheme is implemented, an example embodiment may be configured to perform a waveform analysis of measured voltage-time relationships obtained during at least one of the forward pulse phase, the reverse pulse phase, or both, of a biphasic stimulation pulse, wherein the forward and reverse phases may or may not have the same stimulation parameter settings (e.g., current amplitude, pulse width, etc.). Likewise, ETI parametric data for an implanted lead system may be characterized in a similar manner using other stimulation pulsing schemes depending on the therapy being applied.

Figure 7:
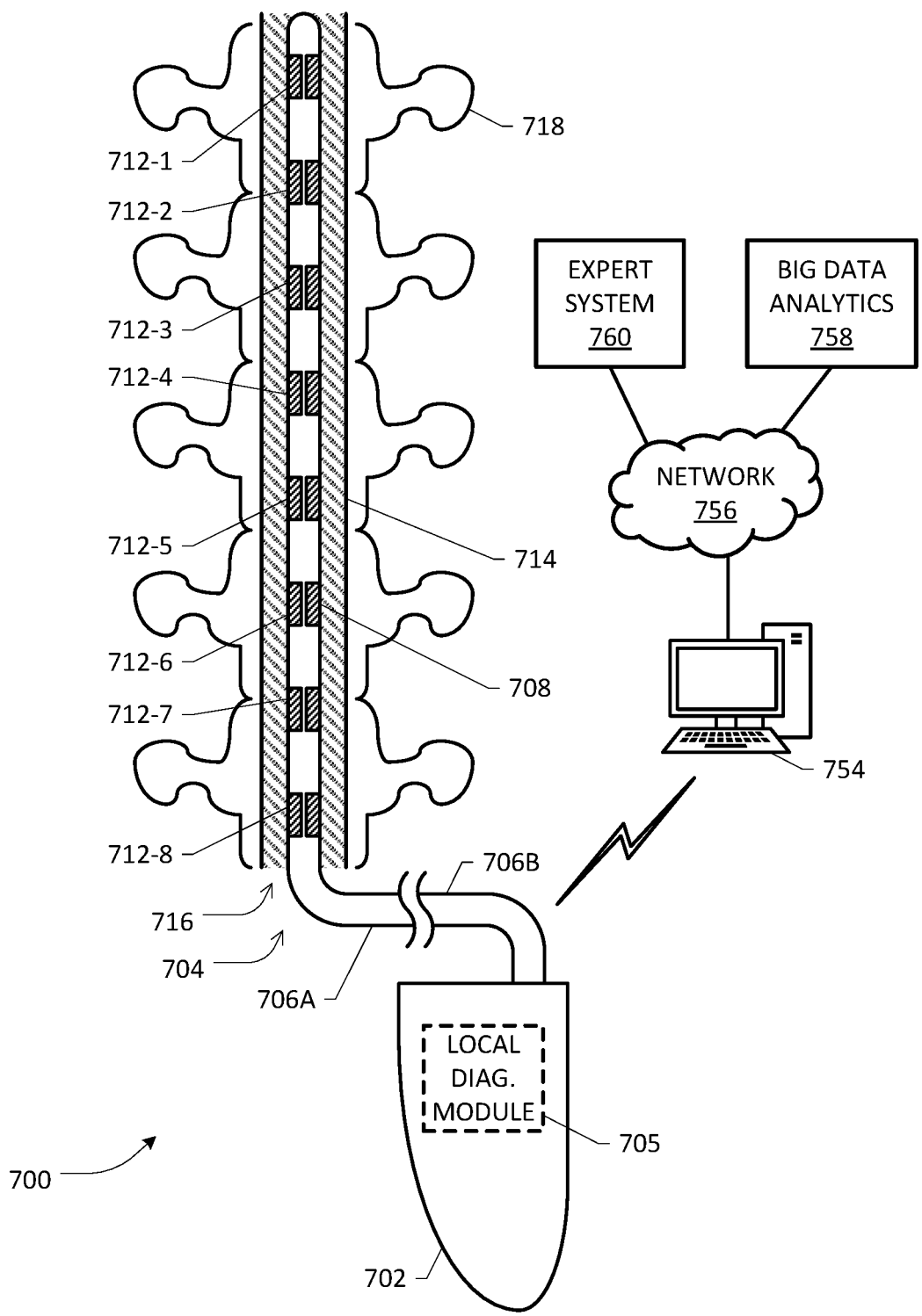
FIG. 7 illustrates an example spinal cord stimulation (SCS) therapy application involving an IPG/IMD and associated lead system having a plurality of electrodes wherein in vivo ETI characterization of different electrodes may be obtained using an embodiment of the present disclosure.

FIG. 7 illustrates an example spinal cord stimulation (SCS) therapy application 700 involving a pulse generator or IMD 702 and associated lead system 704 having a plurality of electrodes 712-1 to 712-8 wherein in vivo ETI characterization of different electrodes may be obtained using an embodiment of the present disclosure. Preferably, the lead system 704 comprises a lead body 706A/B coupled to an implantable lead 708 that may be positioned at a desired target position in an epidural space 716 defined by a plurality of vertebrae of a patient so as to be in close proximity to a nerve tissue of interest, e.g., a spinal cord 714. The implantable lead 708 includes eight electrodes 712-1 to 712-8, which may comprise ring electrodes, segmented or split electrodes, and the like that may be separated from one another by equal or unequal portions of encapsulating material. The implantable lead 708 is connected via lead body 706A/706B to the pulse generator or IMD 702 that includes at least an embodiment of a Kelvin connection scheme that is configured to be operative with suitable diagnostic circuitry 705 of the present disclosure. At least a subset of the electrodes 712-1 to 712-8 may be selectively energized, i.e., stimulated to a target setting in a ramping sequence, or ramped down from a prior therapy setting, whereupon suitable voltage measurements may be taken using a combination of Kelvin connections. For example, in one embodiment electrodes 712-1, 712-4 and 712-8 may be programmed as cathodes or anodes for operation in conjunction with the case or can of the IPG/IMD 702 for providing current stimulation to effectuate an electric field that is spatially distributed over a target portion of the spinal cord 714. An unused electrode, e.g., electrode 712-5, may be used to establish a Kevin connection path on the inactive side of the measurement loop with respect to any of the selected active electrodes 712-1, 712-4 and 712-8 for measuring induced voltages associated therewith.

Although a single implantable lead 708 is exemplified herein, it should be appreciated that a lead system comprising multiple leads, each having a corresponding plurality of electrodes, may be implemented in a stimulation therapy application, wherein appropriate Kelvin connection paths for each lead may be established for different subsets of active and unused electrodes therein across its corresponding electrode/patient interface.

In one example scenario, the diagnostic circuitry 705 of IPG/IMD 702 may therefore be configured to perform, under programmatic control, the following: utilize one of a direct current (DC) blocking stimulation capacitor ($C_{DC}$) terminal and an alternating current (AC) coupling sense capacitor ($C_{SENSE}$) terminal of an inactive electrode, e.g., electrode 712-5 of the implantable lead system 704 as a first Kelvin connection terminal for a voltage measurement with respect to a select active electrode, e.g., electrode 712-4, of the implantable lead system 704; utilize a terminal of an alternating current (AC) coupling sense capacitor ($C_{SENSE}$) coupled to the select active electrode 712-4 as a second Kelvin connection terminal for the voltage measurement; and electrically couple a voltage measurement circuit to the first and second Kelvin connection terminals to measure a voltage associated with the select active electrode for capturing voltage-time functional relationships and facilitating extraction of ETI parametric information relating to the select active electrode in accordance with the teachings herein.

In a further arrangement, the measured voltage-time relationship data may be transmitted via a suitable interface to an external node or device 754 (e.g., a clinician programmer, a patient controller, etc.) that may be configured to execute the ETI parametric extraction in order to reduce the computational load on the IMD/IPG 702. In still further arrangements, external node 754 may be configured as a communication gateway operative to provide the measured voltage-time data and/or ETI parametric data over a network 756 to remote nodes such as expert systems 760, Big Data analytics 758, etc. to facilitate data mining, adaptive biostimulation therapy based on machine learning, artificial intelligence, and the like.

Based on the foregoing Detailed Description, skilled artisans will recognize that embodiments of the present patent disclosure may be advantageously configured to allow the use of the ramping of stimulation parameters during therapy initialization and/or deactivation wherein a plethora of diagnostic measurements and modeling information can be obtained from the patient, the electrodes, and/or the IPG system. By using stimulation parameter ramping during therapy initialization and/or deactivation, a significant benefit may be realized, namely, that the diagnostic information can be obtained without any interference in the normal delivery of therapy to the patient.

In the above-description of various embodiments of the present disclosure, it is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and may not be interpreted in an idealized or overly formal sense expressly so defined herein.

At least some example embodiments are described herein with reference to one or more circuit diagrams/schematics, block diagrams and/or flowchart illustrations. It is understood that such diagrams and/or flowchart illustrations, and combinations of blocks in the block diagrams and/or flowchart illustrations, can be implemented by any appropriate circuitry configured to achieve the desired functionalities. Accordingly, example embodiments of the present disclosure may be embodied in hardware and/or in software (including firmware, resident software, micro-code, etc.) operating in conjunction with suitable processing units or microcontrollers, which may collectively be referred to as "circuitry," "a module" or variants thereof. An example processing unit or a module may include, by way of illustration, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Array (FPGA) circuits, any other type of integrated circuit (IC), and/or a state machine, as well as programmable system devices (PSDs) employing system-on-chip (SoC) architectures that combine memory functions with programmable logic on a chip that is designed to work with a standard microcontroller. Example memory modules or storage circuitry may include volatile and/or nonvolatile memories such as, e.g., random access memory (RAM), electrically erasable/programmable read-only memories (EEPROMs) or UV-EPROMS, one-time programmable (OTP) memories, Flash memories, static RAM (SRAM), etc.

Further, in at least some additional or alternative implementations, the functions/acts described in the blocks may occur out of the order shown in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Furthermore, although some of the diagrams include arrows on communication paths to show a primary direction of communication, it is to be understood that communication may occur in the opposite direction relative to the depicted arrows. Finally, other blocks may be added/inserted between the blocks that are illustrated.

It should therefore be clearly understood that the order or sequence of the acts, steps, functions, components or blocks illustrated in any of the flowcharts depicted in the drawing Figures of the present disclosure may be modified, altered, replaced, customized or otherwise rearranged within a particular flowchart, including deletion or omission of a particular act, step, function, component or block. Moreover, the acts, steps, functions, components or blocks illustrated in a particular flowchart may be inter-mixed or otherwise inter-arranged or rearranged with the acts, steps, functions, components or blocks illustrated in another flowchart in order to effectuate additional variations, modifications and configurations with respect to one or more processes for purposes of practicing the teachings of the present patent disclosure.

Although various embodiments have been shown and described in detail, the claims are not limited to any particular embodiment or example. None of the above Detailed Description should be read as implying that any particular component, element, step, act, or function is essential such that it must be included in the scope of the claims. Reference to an element in the singular is not intended to mean "one and only one" unless explicitly so stated, but rather "one or more." Moreover, the terms "first," "second," and "third," etc. employed in reference to elements or features are used merely as labels, and are not intended to impose numerical requirements, sequential ordering or relative degree of significance or importance on their objects. All structural and functional equivalents to the elements of the above-described embodiments that are known to those of ordinary skill in the art are expressly incorporated herein by reference and are intended to be encompassed by the present claims. Accordingly, those skilled in the art will recognize that the exemplary embodiments described herein can be practiced with various modifications and alterations within the spirit and scope of the claims appended below.

The invention claimed is:

1. A method for characterizing an electrode-tissue interface (ETI) associated with a lead system of an implantable medical device (IMD) implanted in a patient for providing stimulation therapy, the method comprising:
    obtaining voltage measurements at an electrical node associated with at least one electrode implanted in the patient during at least one of a ramping up sequence or a ramping down sequence of a stimulation therapy with respect to the at least one electrode of the lead system;
    obtaining a voltage-to-time relationship based on the voltage measurements; and
    determining electrical load parameters associated with an equivalent circuit of the ETI of the at least one electrode from the voltage-to-time relationship.

2. The method as recited in claim 1, wherein the at least one of a ramping up sequence or a ramping down sequence comprises applying stimulation pulses to the at least one electrode implanted in the patient, the stimulation pulses having stimulation parameters that are incrementally increased to a target therapy setting or incrementally decreased from an applied therapy setting.

3. The method as recited in claim 2, wherein the stimulation pulses comprise constant current pulses with the stimulation parameters including at least one of a pulse width, a current amplitude, and a pulse repetition frequency.

4. The method as recited in claim 3, wherein the determining of electrical load parameters further comprises:
    identifying a step-wise function portion, a linear function portion and a nonlinear function portion of the voltage-to-time relationship;
    determining a bulk patient resistance ($R_S$) of the equivalent ETI circuit associated with the at least one electrode from the substantially step-wise function portion of the voltage-to-time relationship;
    determining at least one of a double-layer capacitance ($C_{DL}$), a direct current (DC) blocking capacitance ($C_{DC}$), and an equivalent series capacitance ($C_{EQ}$) of the equivalent ETI circuit associated with the at least one electrode from the linear function portion of the voltage-to-time relationship; and
    determining a Faradaic resistance ($R_F$) of the equivalent ETI circuit associated with the at least one electrode from one or more piecewise linear approximations of the nonlinear function portion of the voltage-to-time relationship.

5. The method as recited in claim 4, wherein the voltage measurements are obtained from a Kelvin connection terminal operative as the electrical node associated with the at least one electrode.

6. The method as recited in claim 4, wherein the voltage measurements are obtained from a $C_{DC}$ terminal operative as the electrical node associated with the at least one electrode.

7. The method as recited in claim 4, further comprising adjusting the target therapy setting responsive to the electrical load parameters and applying an adjusted target therapy to the patient.

8. The method as recited in claim 4, further comprising providing the electrical load parameters to a data analytics system configured to facilitate an adaptive personalized stimulation therapy for the patient.

9. The method as recited in claim 4, wherein the constant current pulses comprise at least one of monophasic stimulation pulses, biphasic stimulation pulses, burst stimulation pulses and tonic stimulation pulses.

10. The method as recited in claim 4, wherein the stimulation therapy comprises a therapy selected from at least one of a spinal cord stimulation (SCS) therapy, a neuromuscular stimulation therapy, a dorsal root ganglion (DRG) stimulation therapy, a deep brain stimulation (DBS) therapy, a cochlear stimulation therapy, a drug delivery therapy, a cardiac pacemaker therapy, a cardioverter-defibrillator therapy, a cardiac rhythm management (CRM) therapy, an electrophysiology (EP) mapping and radio frequency (RF) ablation therapy, an electroconvulsive therapy (ECT), a repetitive transcranial magnetic stimulation (rTMS) therapy, and a vagal nerve stimulation (VNS) therapy.

11. An implantable medical device (IMD), comprising:
a processing unit;
a lead system comprising one or more leads configured to be implanted proximate to a patient's tissue, wherein each of the leads includes a plurality of electrodes;
a pulse generator module configured to effectuate at least one of a ramp up sequence or a ramp down sequence of a stimulation therapy with respect to at least one of the electrodes of the lead system; and
diagnostic circuitry coupled to the processing unit and the pulse generator module, the diagnostic circuitry configured to:
obtain voltage measurements at an electrical node associated with the at least one electrode implanted in the patient during at least one of the ramping up sequence or the ramping down sequence;
obtain a voltage-to-time relationship based on the voltage measurements; and
determine electrical load parameters associated with an equivalent circuit of an electrode-tissue interface (ETI) of the at least one electrode from the voltage-to-time relationship.

12. The IMD as recited in claim 11, wherein the pulse generator module, responsive to instructions from the processing unit, is operative to apply stimulation pulses to the at least one electrode implanted in the patient, the stimulation pulses having stimulation parameters that are incrementally increased to a target therapy setting during the ramp up sequence or incrementally decreased from an applied therapy setting during the ramp down sequence.

13. The IMD as recited in claim 12, wherein the stimulation pulses comprise constant current pulses with the stimulation parameters including at least one of a pulse width, a current amplitude, and a pulse repetition frequency.

14. The IMD as recited in claim 13, wherein the diagnostic circuitry is further configured to perform following operations responsive to instructions from the processing unit:
identify a step-wise function portion, a linear function portion and a nonlinear function portion of the voltage-to-time relationship;
determine a bulk patient resistance ($R_S$) of the equivalent ETI circuit associated with the at least one electrode from the substantially step-wise function portion of the voltage-to-time relationship;
determine at least one of a double-layer capacitance ($C_{DL}$), a direct current (DC) blocking capacitance ($C_{DC}$), and an equivalent series capacitance ($C_{EQ}$) of the equivalent ETI circuit associated with the at least one electrode from the linear function of the voltage-to-time relationship; and
determine a Faradaic resistance ($R_F$) of the equivalent ETI circuit associated with the at least one electrode from one or more piecewise linear approximations of the nonlinear function portion of the voltage-to-time relationship.

15. The IMD as recited in claim 14, wherein the at least one electrode is coupled to an alternating current (AC) coupling sense capacitor ($C_{SENSE}$) operative to support a Kelvin connection terminal that is configured as the electrical node for obtaining the voltage measurements associated with the at least one electrode.

16. The IMD as recited in claim 14, wherein the at least one electrode is coupled to a DC blocking capacitor ($C_{DC}$) terminal operative as the electrical node for obtaining the voltage measurements associated with the at least one electrode.

17. The IMD as recited in claim 14, further comprising a communications interface for providing the electrical load parameters to a data analytics system configured to facilitate an adaptive personalized stimulation therapy for the patient.

18. The IMD as recited in claim 14, wherein the stimulation therapy comprises a therapy selected from at least one of a spinal cord stimulation (SCS) therapy, a neuromuscular stimulation therapy, a dorsal root ganglion (DRG) stimulation therapy, a deep brain stimulation (DBS) therapy, a cochlear stimulation therapy, a drug delivery therapy, a cardiac pacemaker therapy, a cardioverter-defibrillator therapy, a cardiac rhythm management (CRM) therapy, an electrophysiology (EP) mapping and radio frequency (RF) ablation therapy, an electroconvulsive therapy (ECT), a repetitive transcranial magnetic stimulation (rTMS) therapy, and a vagal nerve stimulation (VNS) therapy.

19. The IMD as recited in claim 14, wherein the constant current pulses comprise at least one of monophasic stimulation pulses, biphasic stimulation pulses, burst stimulation pulses and tonic stimulation pulses.

20. A method for determining electrical load parameters associated with a lead system of an implantable medical device (IMD) implanted in a patient for providing stimulation therapy, the method comprising:
obtaining a target therapy setting for the IMD implanted in the patient with respect to a stimulation therapy, the target therapy setting comprising one or more stimulation parameters to be applied to one or more electrodes of the lead system for stimulating the patient's tissue;
ramping up to the target therapy setting by incrementally varying at least one stimulation parameter and applying stimulation pulses to an electrode at a plurality of incrementally increased values of the varying stimulation parameter;
during ramp-up to the target therapy setting, obtaining in vivo voltage measurements associated with the stimulated electrode at each of the incrementally increased values of the varying stimulation parameter; and
obtaining electrical load parameters associated with an equivalent circuit of an electrode-tissue interface (ETI) of the stimulated electrode based on the in vivo voltage measurements.

21. The method as recited in claim 20, wherein the stimulation pulses applied to the patient during the ramp-up comprise constant current pulses having the varying stimulation parameter including at least one of a pulse width, a current amplitude, and a pulse repetition frequency.

22. The method as recited in claim 21, wherein the obtaining of electrical load parameters further comprises:
at each value of the varying stimulation parameter, determining a voltage functional relationship between the in vivo voltage measurements and a time variable;
identifying a step-wise function portion, a linear function portion and a nonlinear function portion of the voltage functional relationship;
determining a bulk patient resistance ($R_S$) of the equivalent ETI circuit associated with the stimulated electrode from the substantially step-wise function portion of the voltage functional relationship;
determining at least one of a double-layer capacitance ($C_{DL}$), a direct current (DC) blocking capacitance ($C_{DC}$), and an equivalent series capacitance ($C_{EQ}$) of the equivalent ETI circuit associated with the stimulated electrode from the linear function of the voltage functional relationship; and
determining a Faradaic resistance ($R_F$) of the equivalent ETI circuit associated with the stimulated electrode from one or more piecewise linear approximations of the nonlinear function portion of the voltage functional relationship.

23. The method as recited in claim 22, wherein the in vivo voltage measurements are obtained from a Kelvin connection node associated with the stimulated electrode.

24. The method as recited in claim 22, further comprising determining a functional relationship between the electrical load parameters of the ETI of the stimulated electrode and the varying stimulation parameter.

25. The method as recited in claim 22, wherein the constant current pulses comprise at least one of monophasic stimulation pulses, biphasic stimulation pulses, burst stimulation pulses and tonic stimulation pulses.

* * * * *